(12) United States Patent
Infantino et al.

(10) Patent No.: US 7,316,674 B2
(45) Date of Patent: Jan. 8, 2008

(54) INCONTINENCE ARTICLE HAVING A BUMPER

(76) Inventors: Stacey A. Infantino, P.O. Box 132, South Cairo, NY (US) 12482; Tara J. Valentin, 1980 Western Ave., Apt. 932, Albany, NY (US) 12203

( * ) Notice: Subject to any disclaimer, the term of this patent is extended or adjusted under 35 U.S.C. 154(b) by 0 days.

(21) Appl. No.: 10/081,938

(22) Filed: Feb. 22, 2002

(65) Prior Publication Data

US 2002/0193728 A1   Dec. 19, 2002

Related U.S. Application Data

(63) Continuation-in-part of application No. 09/871,717, filed on Jun. 1, 2001.

(51) Int. Cl.
*A61F 13/15*  (2006.01)

(52) U.S. Cl. .................. 604/385.16; 604/385.01; 604/385.31; 604/385.28; 604/385.11; 604/385.25; 604/385.23

(58) Field of Classification Search ........... 604/385.19, 604/385.28, 385.01, 385.31
See application file for complete search history.

(56) References Cited

U.S. PATENT DOCUMENTS

| | | | |
|---|---|---|---|
| 1,998,140 A | 4/1935 | Loew | |
| 2,621,327 A * | 12/1952 | Amoroso | .......................... 2/467 |
| 2,630,120 A | 3/1953 | Nielson | |
| 4,578,072 A | 3/1986 | Lancaster | |
| 4,738,677 A * | 4/1988 | Foreman | ................. 604/385.27 |
| 4,938,753 A | 7/1990 | Van Gompel et al. | |
| 5,106,385 A | 4/1992 | Allen et al. | |
| D330,080 S | 10/1992 | Norberg | |
| H1440 H | 5/1995 | New et al. | |
| 5,531,730 A | 7/1996 | Dreier | |
| 5,558,659 A | 9/1996 | Sherrod et al. | |
| 5,558,660 A * | 9/1996 | Dreier | .................... 604/385.19 |
| 5,795,347 A * | 8/1998 | Roe et al. | .............. 604/385.19 |
| 5,858,012 A | 1/1999 | Yamaki et al. | |
| 5,989,236 A | 11/1999 | Roe et al. | |
| 6,258,076 B1 * | 7/2001 | Glaug et al. | ................. 604/387 |
| 6,264,639 B1 * | 7/2001 | Sauer | ................... 604/385.101 |
| 6,280,426 B1 | 8/2001 | Turner et al. | |
| 6,425,889 B1 * | 7/2002 | Kitaoka et al. | ......... 604/385.01 |
| 6,450,997 B1 * | 9/2002 | Seitz et al. | ............. 604/385.01 |
| 6,506,185 B1 * | 1/2003 | Sauer et al. | ............ 604/385.01 |

\* cited by examiner

*Primary Examiner*—Jacqueline F. Stephens
(74) *Attorney, Agent, or Firm*—Hoffman, Warnick & D'Alessandro LLXC

(57) ABSTRACT

An incontinence article having a bumper is provided. In particular, the present invention provides an incontinence article having a bumper positioned along a top edge thereof. The bumper prevents waste from leaking out of the article. The bumper could optionally be used in conjunction with a front guard and/or a back guard.

22 Claims, 22 Drawing Sheets

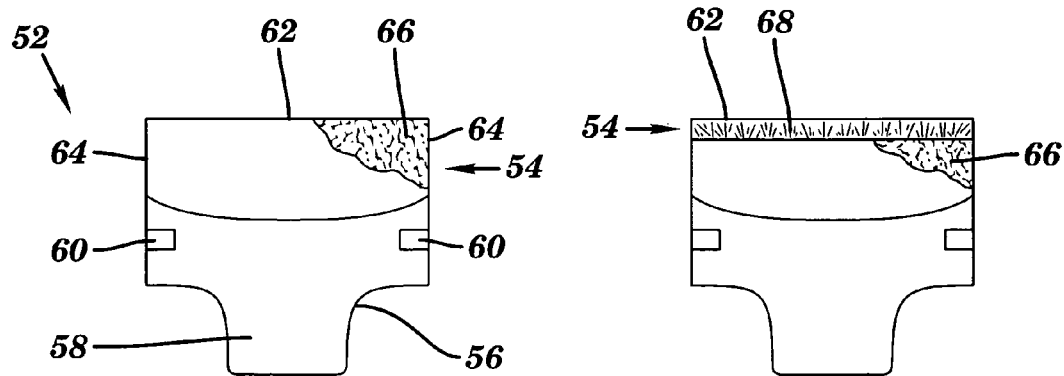
*FIG. 3A*  *FIG. 3B*
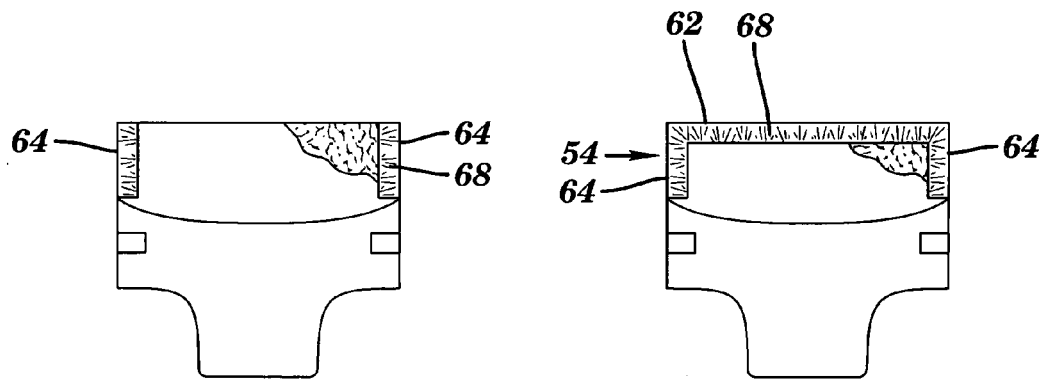
*FIG. 3C*  *FIG. 3D*
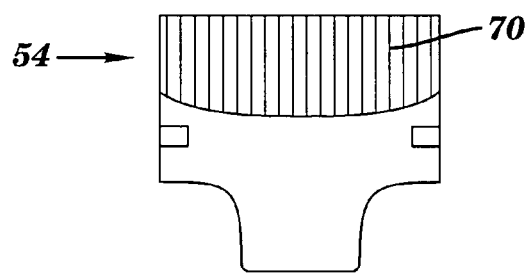
*FIG. 3E*

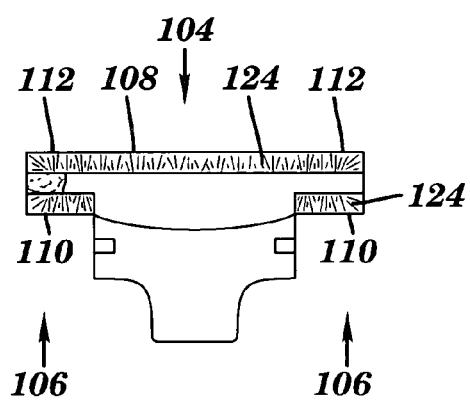
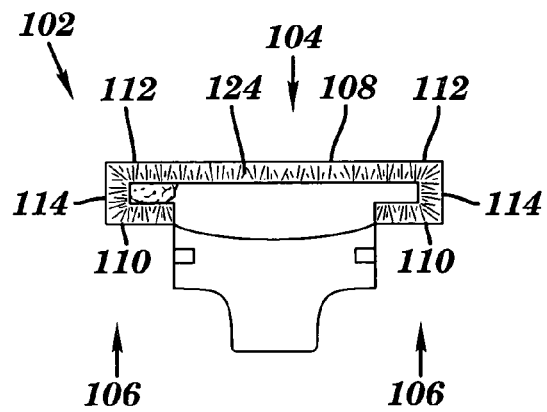
FIG. 5G    FIG. 5H
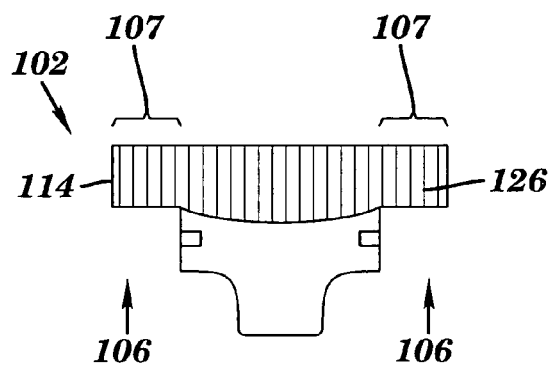
FIG. 5I

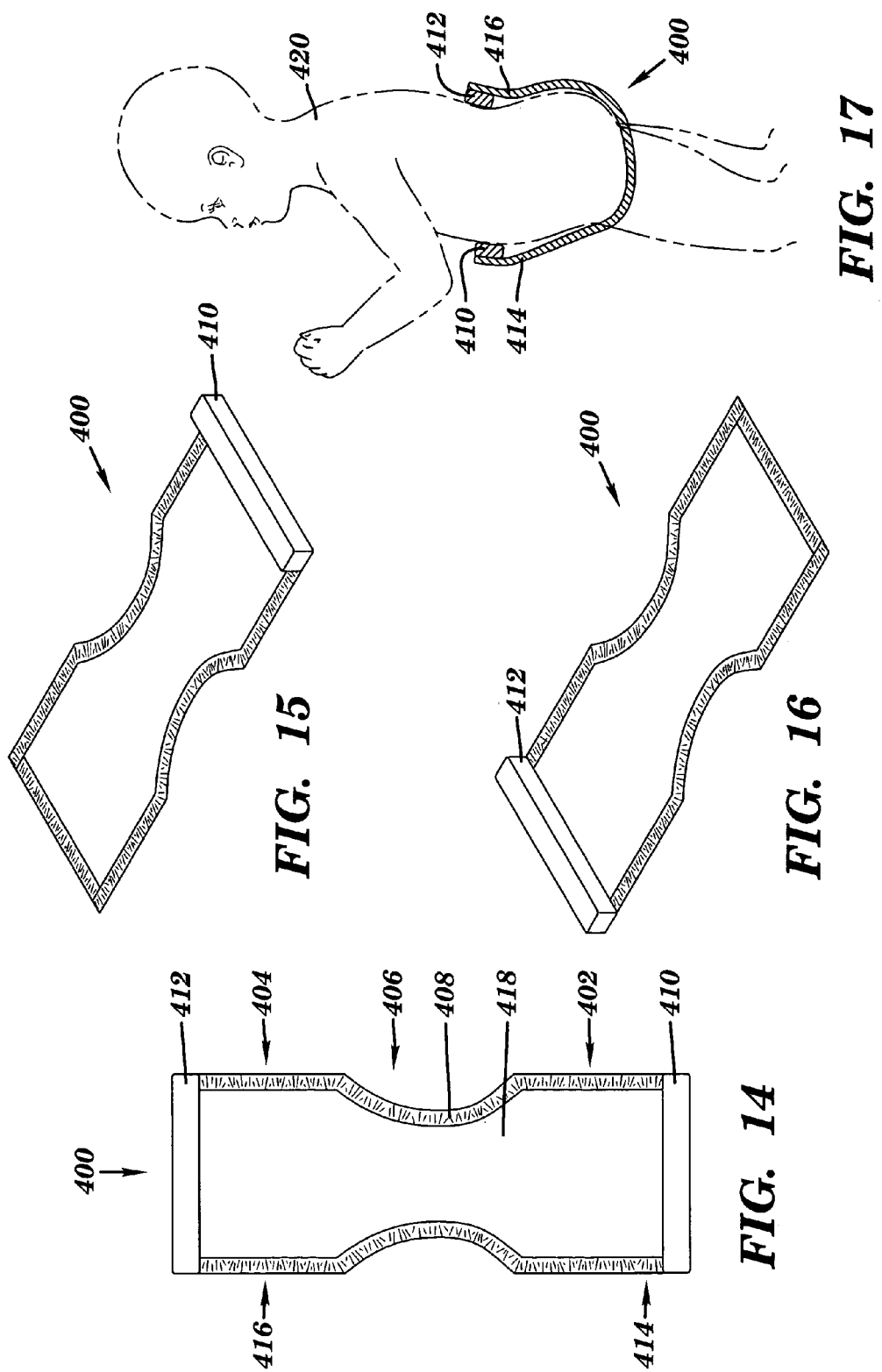

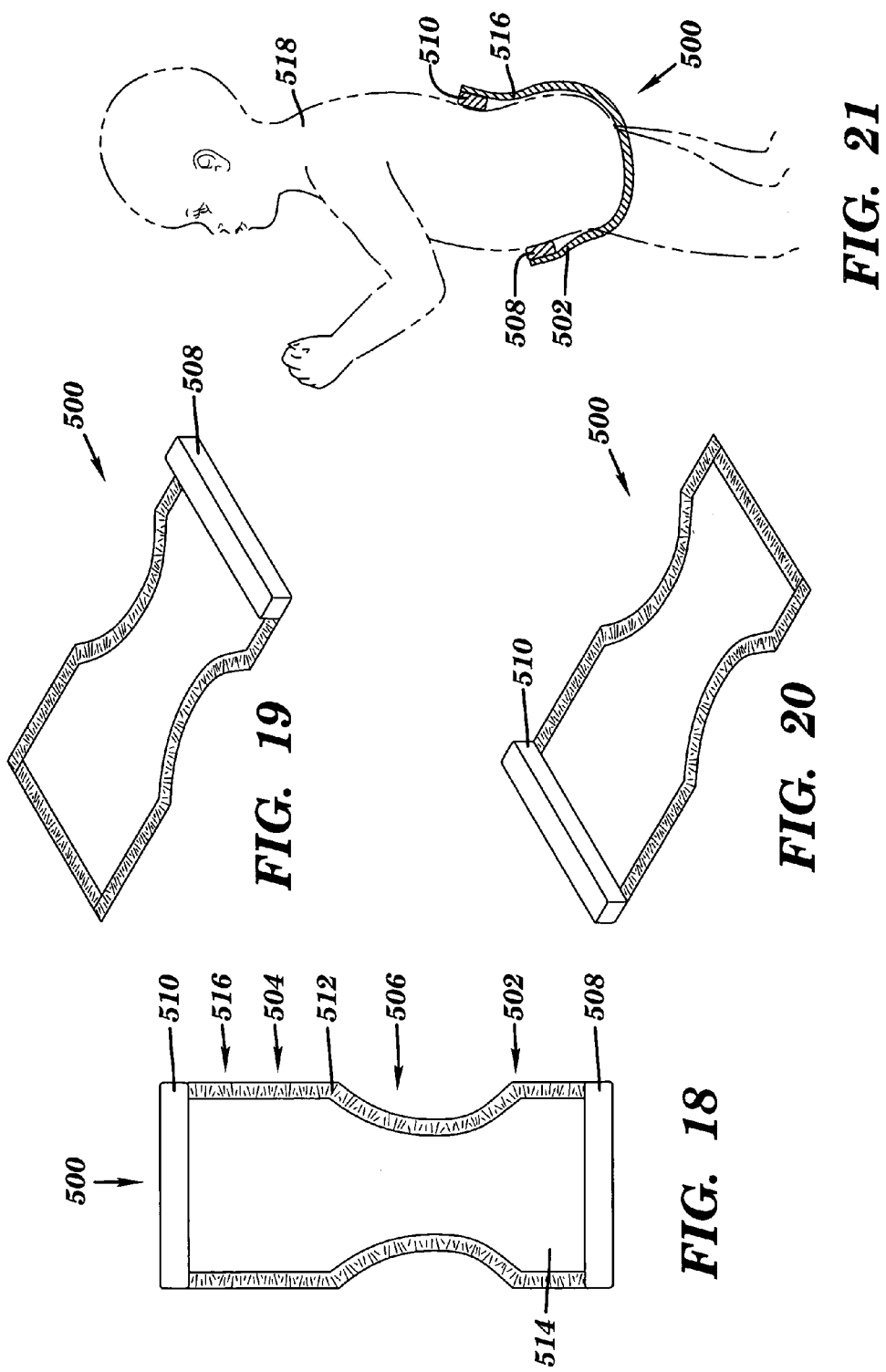

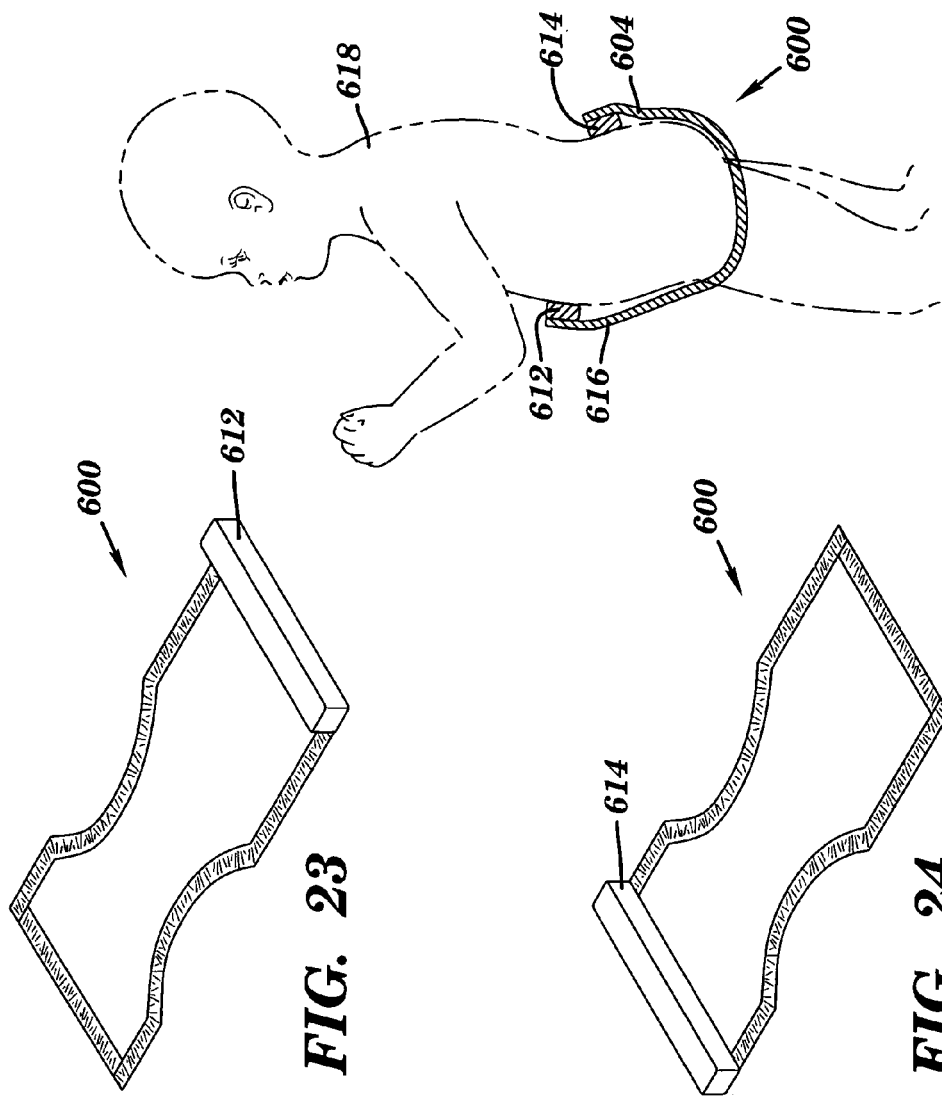
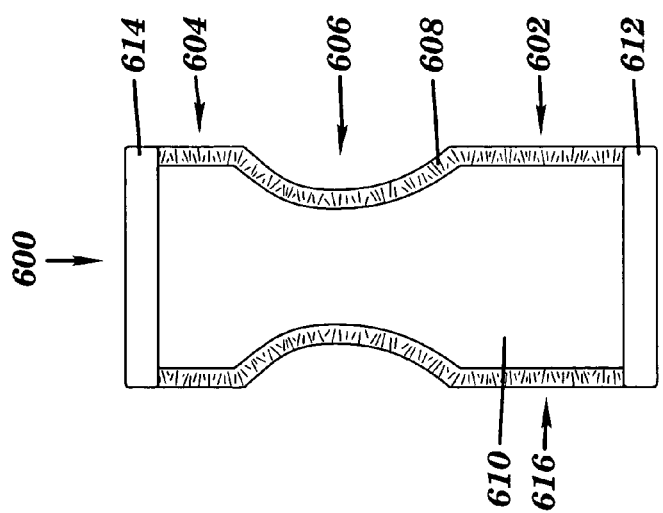
FIG. 25
FIG. 23
FIG. 24
FIG. 22

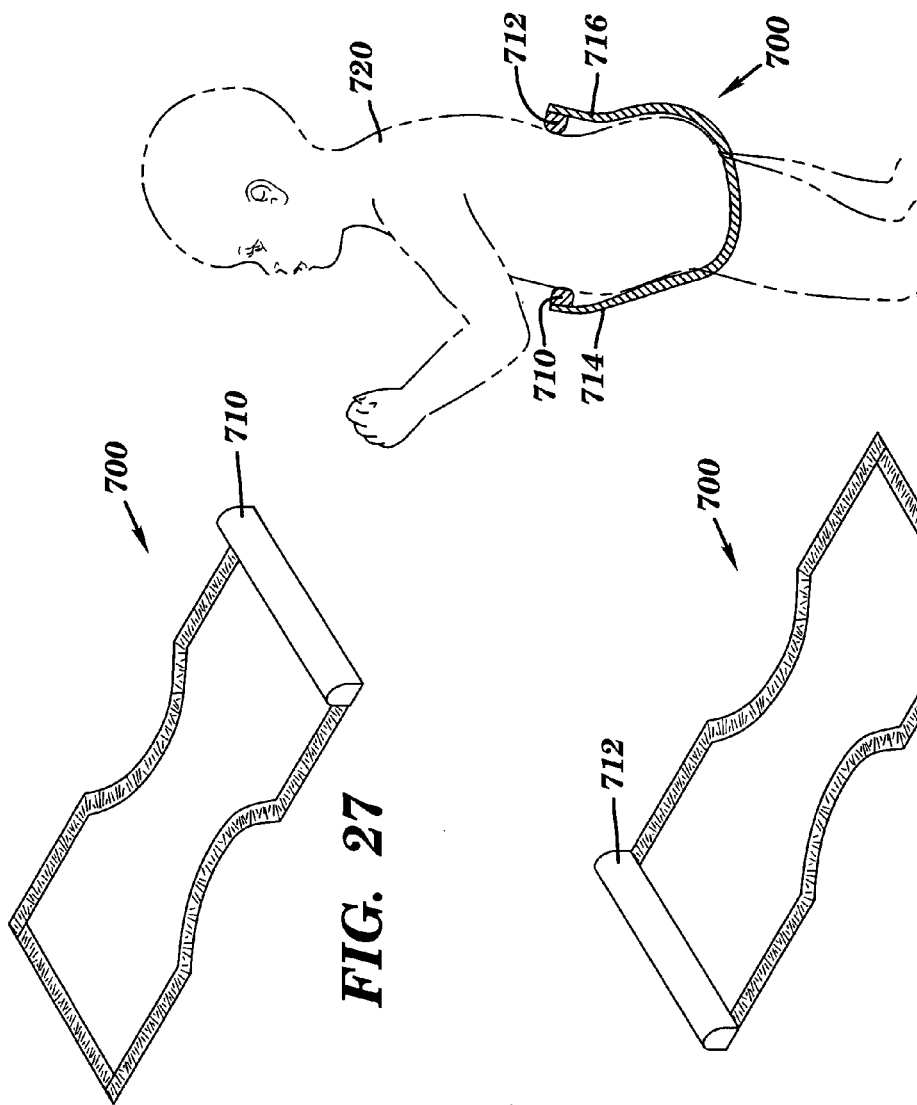
FIG. 29
FIG. 27
FIG. 28
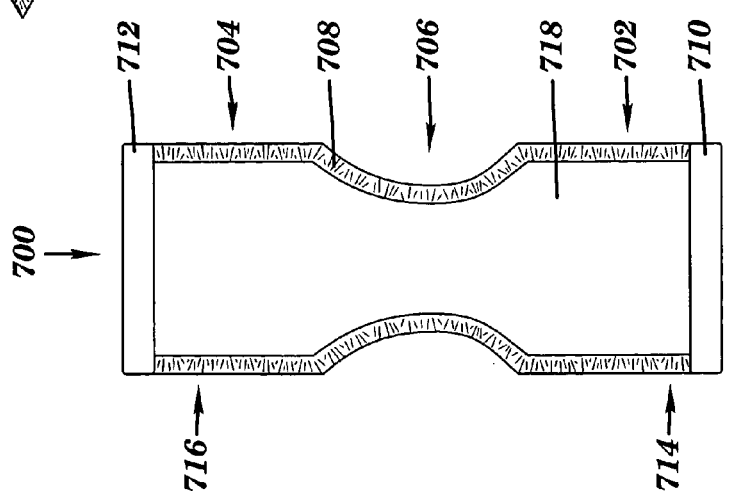
FIG. 26

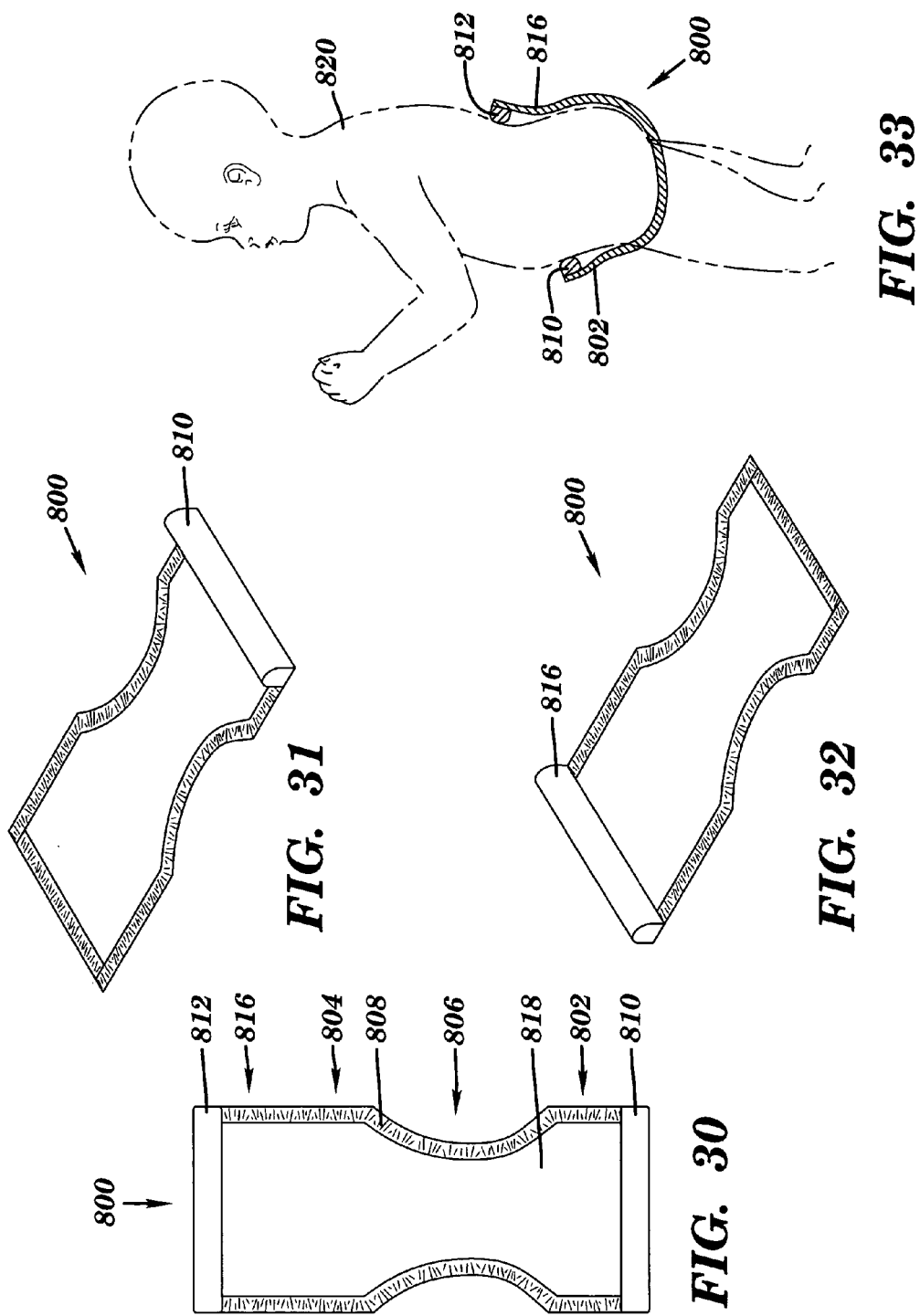

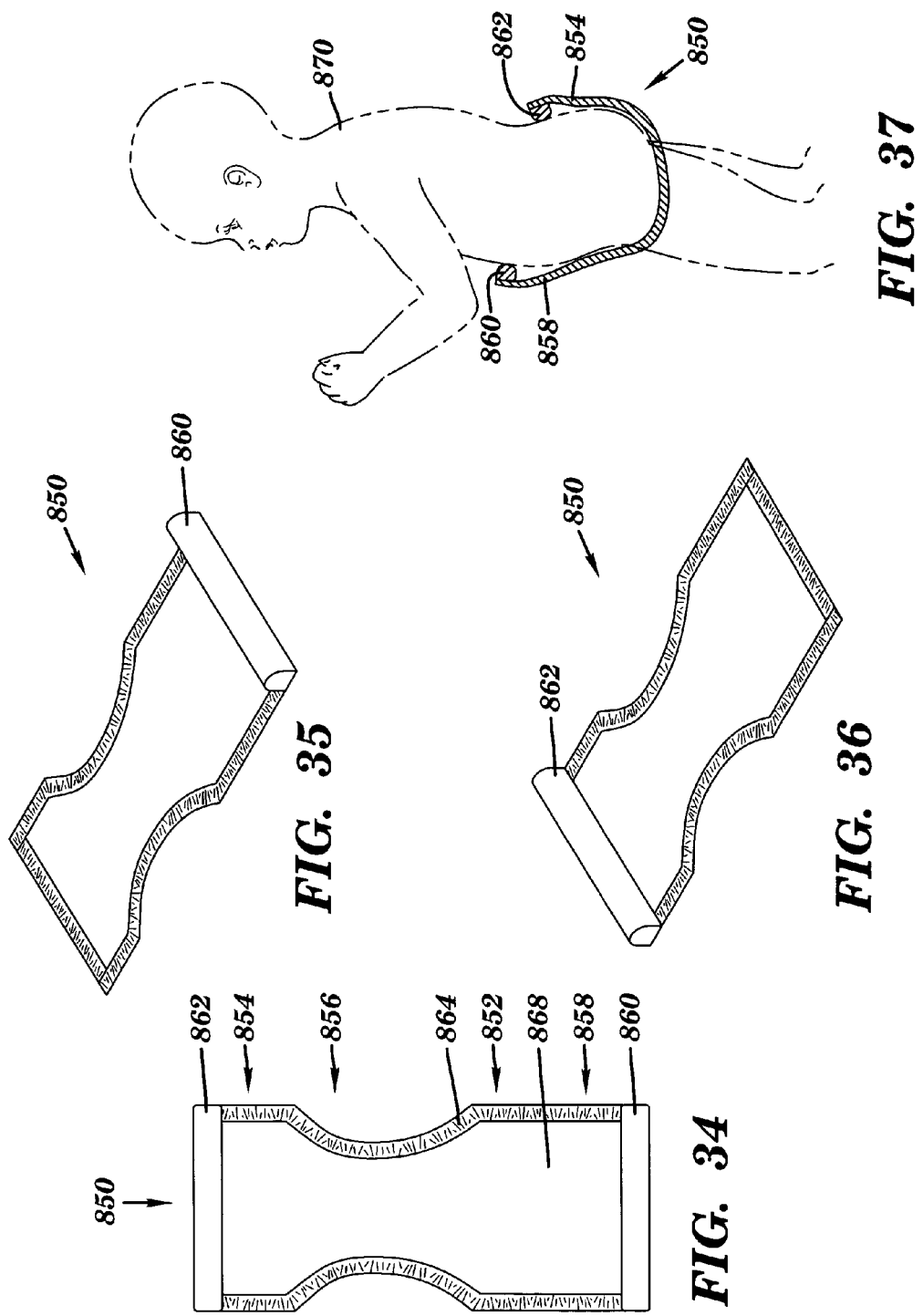

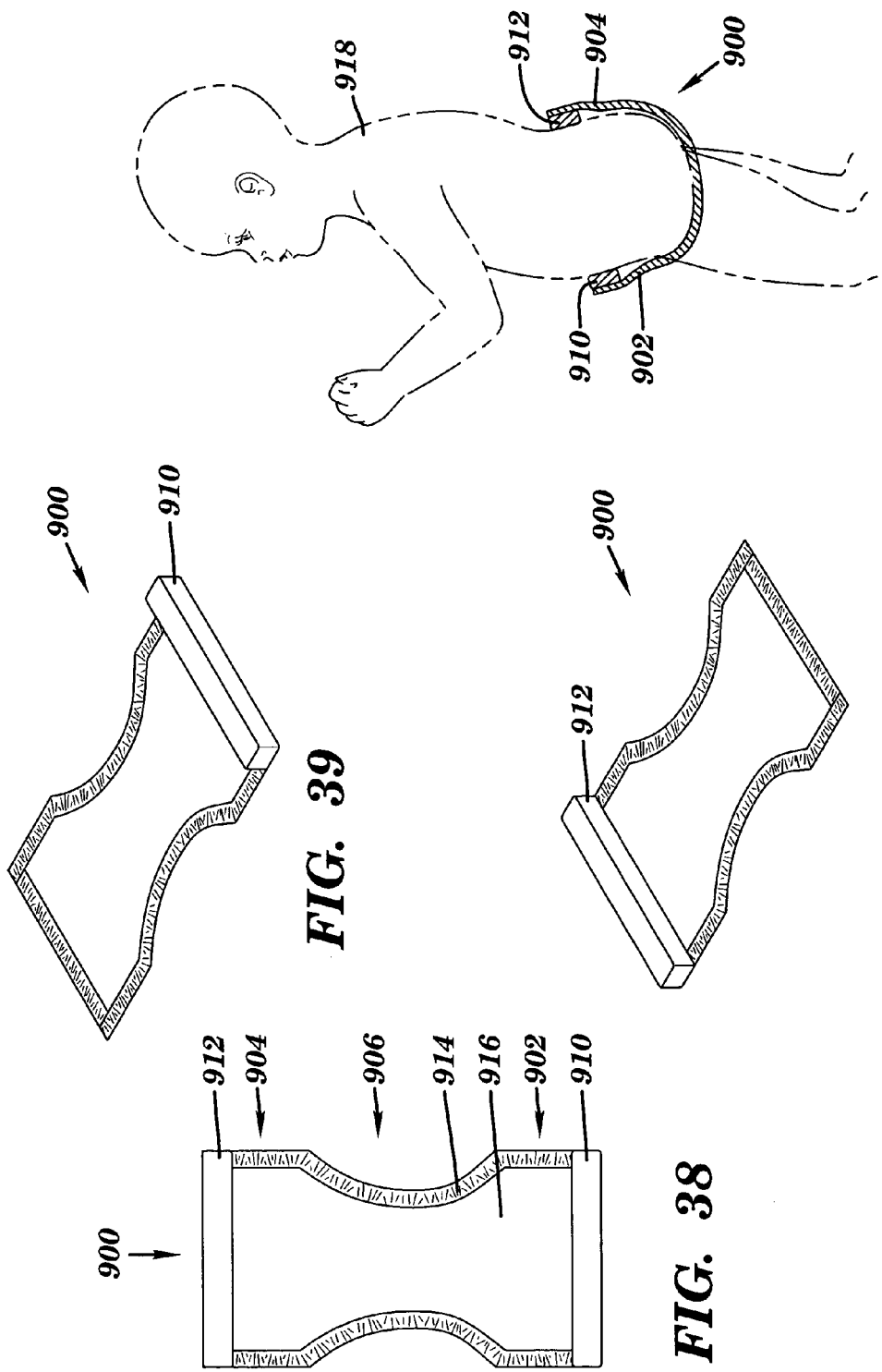

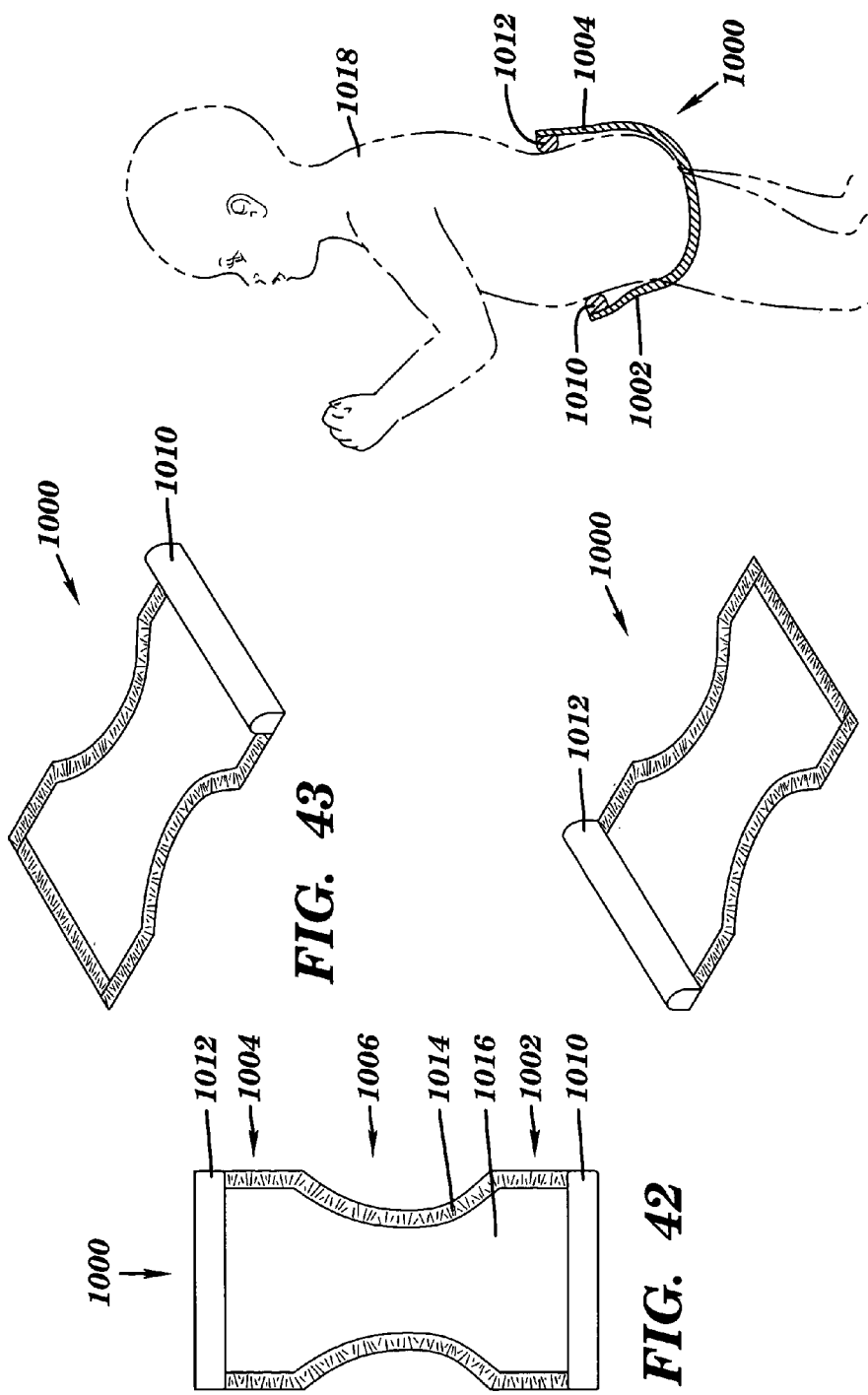

INCONTINENCE ARTICLE HAVING A BUMPER

CROSS-REFERENCE TO RELATED APPLICATIONS

This application is a continuation-in-part of co-pending U.S. application Ser. No. 09/871,717, filed on Jun. 1, 2001 and entitled "Incontinence Article Having a Back Guard," herein incorporated by reference.

BACKGROUND OF THE INVENTION

1. Technical Field

The present invention generally relates to an incontinence article having a bumper for protecting the clothing of a user. More particular, the present invention relates to an incontinence article for children or adults in which a bumper is positioned on/attached to the back and/or front of the article to prevent waste leakage.

2. Background Art

The use of disposable incontinence articles is gaining widespread use in the care of both children and adults. A typical incontinence article (e.g., a diaper) is a multilayered composite structure that includes a liquid permeable body-side layer, a liquid impermeable outer cover, and an absorbent material positioned between the outer cover and the body-side liner.

Children's diapers are generally flat garments intended to be fit around a child while lying down. Adult incontinence articles are usually constructed with multiple layers similar to a child's diaper, but are often made thinner and narrower for improved discreteness. Moreover, many adult incontinence articles are constructed to be slipped on by a user similar to a pair of shorts However, a problem unrecognized by existing incontinence articles is that, when worn, waste products often leak to the back torso area of the user. This is generally caused, for example, when the user shifts between a seated position and a standing position, or between a seated position and a lying position. In addition, due to new guidelines set forth by the Sudden Infant Death Syndrome (SIDS) Alliance and the American Academy of Pediatrics, children are increasingly being placed on their backs' to sleep, which causes leakage. When waste products leak, the user's back often becomes soiled and his/her clothing becomes ruined.

Heretofore, attempts have been made to reduce leaking in incontinence articles by improving the absorbent material and/or improving the fit of the article to the user (e.g., by providing additional or improved elastic systems). However, none of these systems truly prevent waste from leaking to the back of the user. One such example is shown in U.S. Pat. No. 5,858,012 to Yamaki et al., herein incorporated by reference. Yamaki et al. provide a short band of elastic extending from a rear portion of a diaper. However, due to the lack of absorbent material around the band of elastic, as well as the short length thereof, the user's back and clothes are still at risk.

In view of the forgoing, there exists a need for an incontinence article having bumper. A further need exists for such a bumper to be positioned on/attached to the back and/or front of the article. In addition, a need exists for an incontinence article having a bumper in conjunction with a high front and/or high back.

SUMMARY OF THE INVENTION

The present invention overcomes the problems of existing devices by providing an incontinence article having a front portion, a rear portion, and a bumper positioned on/attached to the front and/or rear portion. The bumper can optionally be used in conjunction with a front guard and/or a back guard.

According to a first aspect of the present invention, an incontinence article is provided. The article comprises: (1) a front portion; (2) a rear portion joined to the front portion; and (3) a bumper positioned on at least one of the front portion and the rear portion.

According to a second aspect of the present invention, an incontinence article is provided. The article comprises: (1) a front portion having a front guard extending therefrom; (2) a rear portion having a back guard extending therefrom; (3) a crotch portion between the front portion and the rear portion; and (4) a bumper positioned on at least one of the front guard and the back guard.

According to a third aspect of the present invention, an incontinence article is provided. The article comprises: (1) a front portion; (2) a rear portion having a back guard extending therefrom; (3) a crotch portion between the front portion and the rear portion; and (4) a bumper positioned on at least one of the front portion and the back guard.

According to a fourth aspect of the present invention, an incontinence article is provided. The article comprises: (1) a front portion having a front guard extending therefrom; (2) a rear portion; (3) a crotch portion between the front portion and the rear portion; and (4) a bumper positioned on at least one of the front guard and the rear portion.

Therefore, a preferred embodiment of the present invention provides an incontinence article having a bumper. The article includes a front portion, a rear portion joined to the front portion, and a bumper positioned on/attached to the front and/or the back portion. The bumper could optionally be used in conjunction with a front guard and/or back guard.

BRIEF DESCRIPTION OF THE DRAWINGS

These and other features and advantages of this invention will be more readily understood from the following detailed description of the various aspects of the invention taken in conjunction with the accompanying drawings in which:

FIGS. 3A-E depict front views of an incontinence article having a back guard.

FIGS. 5A-I depict front views of an incontinence article having a back guard.

FIG. 14 depicts an incontinence article having a front guard, a back guard, a front bumper and a back bumper.

FIG. 15 depicts an incontinence article having a front guard, a back guard and a front bumper.

FIG. 16 depicts an incontinence article having a front guard, a back guard and a back bumper.

FIG. 17 depicts the incontinence article of FIG. 14 when worn by a user.

FIG. 18 depicts an incontinence article having a back guard, a front bumper and a back bumper.

FIG. 19 depicts an incontinence article having a back guard and a front bumper.

FIG. 20 depicts an incontinence article having a back guard and a back bumper.

FIG. 21 depicts the incontinence article of FIG. 18 when worn by a user.

FIG. 22 depicts an incontinence article having a front guard, a front bumper and a back bumper.

FIG. 23 depicts an incontinence article having a front guard and a front bumper.

FIG. 24 depicts an incontinence article having a front guard and a back bumper.

FIG. 25 depicts the incontinence article of FIG. 22 when worn by a user.

FIG. 26 depicts an incontinence article having a front guard, a back guard, a front bumper and a back bumper.

FIG. 27 depicts an incontinence article having a front guard, a back guard and a front bumper.

FIG. 28 depicts an incontinence article having a front guard, a back guard and a back bumper.

FIG. 29 depicts the incontinence article of FIG. 26 when worn by a user.

FIG. 30 depicts an incontinence article having a back guard, a front bumper and a back bumper.

FIG. 31 depicts an incontinence article having a back guard and a front bumper.

FIG. 32 depicts an incontinence article having a back guard and a back bumper.

FIG. 33 depicts the incontinence article of FIG. 30 when worn by a user.

FIG. 34 depicts an incontinence article having a front guard, a front bumper and a back bumper.

FIG. 35 depicts an incontinence article having a front guard and a front bumper.

FIG. 36 depicts an incontinence article having a front guard and a back bumper.

FIG. 37 depicts the incontinence article of FIG. 34 when worn by a user.

FIG. 38 depicts an incontinence article having a front bumper and a back bumper.

FIG. 39 depicts an incontinence article having a front bumper.

FIG. 40 depicts an incontinence article having a back bumper.

FIG. 41 depicts the incontinence article of FIG. 38, when worn by a user.

FIG. 42 depicts an incontinence article having a front bumper and a back bumper.

FIG. 43 depicts an incontinence article having a front bumper.

FIG. 44 depicts an incontinence article having a back bumper.

FIG. 45 depicts the incontinence article of FIG. 42 when worn by a user.

Figure 1:
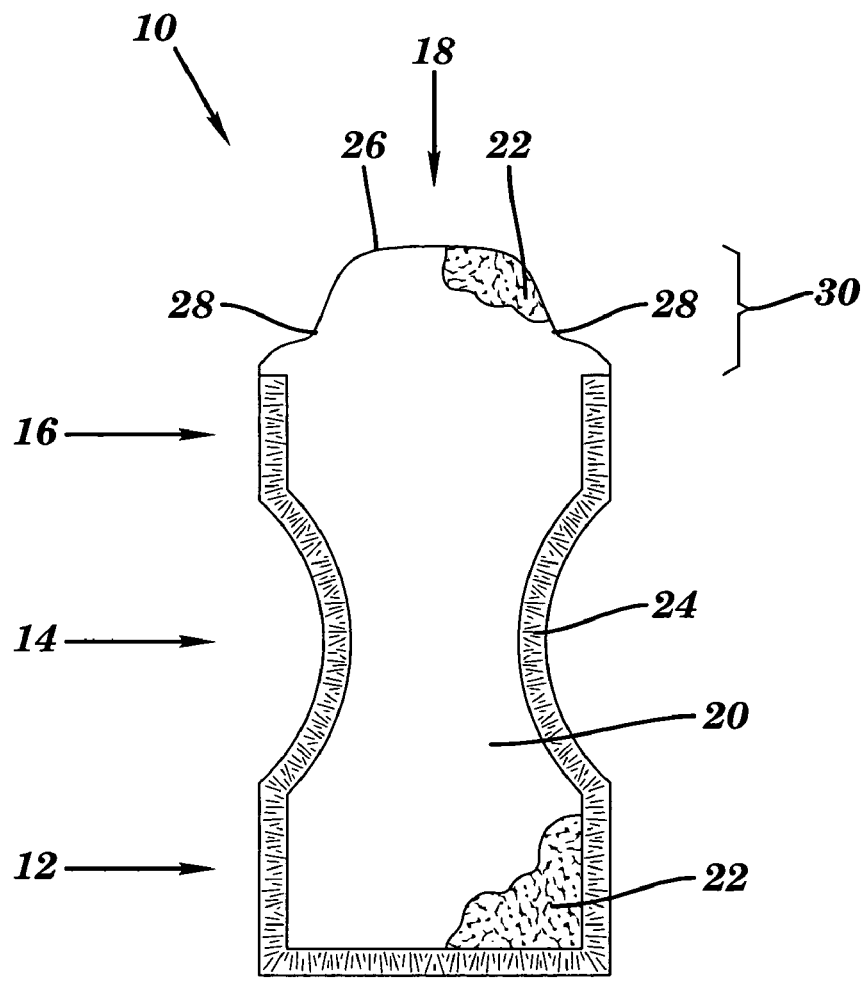
FIG. 1 depicts a plan view of an unfolded incontinence article, according to the present invention.

It is noted that the drawings of the invention are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE DRAWINGS

Referring now to FIG. 1, an incontinence article 10 according to the present invention is shown. Article 10 is a diaper, or the like, and can be used by children or adults. Article 10 generally includes: front portion 12 for contacting a front side of a user; rear portion 16 for contacting a rear side of a user; crotch portion 14 joining the front portion to the rear portion for contacting a crotch of a user; and back guard 18. As shown, back guard 18 extends from rear portion 16 and can be connected to rear portion 16 as an attachment or can be formed as a continuous body with rear portion 16 (as shown in FIG. 1).

The construction of article 10 is well known in the art. Specifically, article 10 preferably includes three layers: (1) a liquid permeable body-side layer 20; (2) a non-permeable outer cover (not shown in FIG. 1); and an absorbent material 22 between the outer cover and the body-side layer 20. Liquid permeable body-side layer 20 can be any soft, flexible, porous sheet, which allows fluids to pass therethrough. For example, body-side layer 20 could be: (1) a non-woven web or sheet of wet strength tissue paper; (2) a spunbonded, meltblown, or bonded-carded web composed of synthetic polymer filaments, such as polyproplyene, polyethylene, polyesters or the like; or (3) a web or natural polymer filaments such as rayon or cotton. Outer cover is preferably a liquid impermeable material such as, for example, a web or sheet of plastic film. Absorbent material 22 is preferably a material (e.g., wood pulp fluff) capable of absorbing and retaining fluids. These and other possible materials for article 10 are shown and described in U.S. Pat. No. 4,938,753 to Van Gompel et al. and U.S. Pat. No. 5,558,659 to Sherrod et al., both of which are herein incorporated by reference. However, it should be understood that the materials used to construct the incontinence articles of the present invention are for illustrative purposes only and are not intended to be a limiting feature. Along a periphery of the front portion 12, crotch portion 14, and rear portion 16 is retention system 24. Retention system 24, which is preferably elastic, allows article 10 to be snugly fitted on the user and helps prevent waste products from leaking out of the sides.

Back guard 18 will be described in further detail below, but similar to portions 12, 14, and 16 of article 10, includes a liquid permeably body-side layer, a non-permeable outer cover, and an absorbent material there between. Moreover, as indicated above, back guard 18 extends from rear portion 16 to a middle back area of a user. Because the users will vary in size, back guard 18 can be made any length capable of extending to a middle back area of an intended user. Thus, for example, back guard 18 can have any length 30 anywhere from approximately 1.0 to 24.0 inches. Preferably, back guard 18 has a length 30 of approximately at least 1.0 inches, and more preferably, a length 30 of approximately 1.0 to 10.0 inches. In an alternative embodiment, back guard 18 has a length 30 of at least 1.5 inches, and more preferably, a length 30 of approximately 1.5 to 10.0 inches. In an alternative embodiment, back guard 18 preferably has a length 30 of approximately at least 2.0 inches, and more preferably, a length 30 of approximately 2.0 to 10.0 inches. In an alternative embodiment, back guard 18 has a length 30 of at least approximately 3.0 inches, and more preferably, a length 30 of approximately 3.0 to 10.0 inches. In another embodiment back guard 18 has a length 30 of at least approximately 4.0, and more preferably, a length of approximately 4.0 to 10.0 inches. In an alternative embodiment, back guard 18 preferably has a length 30 of approximately at least 5.0 inches, and more preferably, a length 30 of approximately 5.0 to 10.0 inches. In an alternative embodiment, back guard 18 preferably has a length 30 of approximately at least 6.0 inches, and more preferably, a length 30 of approximately 6.0 to 10.0 inches. In an alternative embodiment, back guard 18 preferably has a length 30 of approximately at least 7.0 inches, and more preferably, a length 30 of approximately 7.0 to 10.0 inches. Accordingly, it should be realized that length 30 of back guard 18 can be of any value or range of values between 1.0 and 24.0 inches. These possible lengths and/or ranges of lengths are intended to apply to all embodiments of the present invention described herein.

The back guards of the various embodiments of the present invention (as further discussed below) are intended to reach/extend to approximately the middle back area of the user without having to adjust (e.g., lower) the front portion of the article. With previous articles, the only way to raise the height of the back is to pull the back portion upward while pulling the front portion downward (i.e., toward the crotch of the user). However, when pulling the front portion downward, the user loses protection on his/her front torso areas. Thus, causing the same problems for the front torso area that occurred for the back torso area. In addition, it is often not possible to maintain the back portion in the elevated position because as the user shifted positions, the back portion falls back to its "normal" resting position about the small of the user's back.

Referring now to FIGS. 2A-E, an incontinence article 32 having a back guard 34 in a closed position (when not worn by a user), according to a first embodiment of the present invention is shown. As depicted, back guard 34 includes top portion 42, curved opposing side portions 44, and absorbent material 46. Moreover, as described above, article 32 includes an impermeable outer cover 38 (shown on front portion 36). Rear portion and front portion 36 are placed in a closed position using any means known in the art. For example, tabs 40 could be used to further couple front portion 36 to rear portion. Tabs 40 could use adhesive, hooks and loops, etc. Moreover, the quantity of tabs shown is not intended to be limiting. For example, article 32 could include four tabs. As indicated above, back guard 34 is intended to extend from rear portion to the middle back area of the user. As shown, when placed in a closed position without a user, back guard 34 extends well above front portion 36. In previous articles, the rear portion and front portion 36 were approximately parallel when placed in a closed position without a user. Thus, the only way to extend the previous article to the middle back area is to pull the front portion downward while pulling the back portion upward.

Figure 2A:
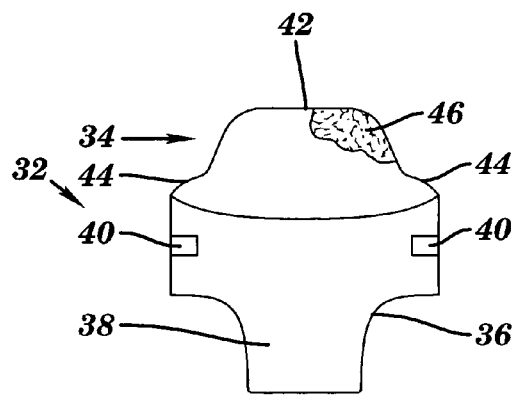
FIGS. 2A-E depict front views of an incontinence article having a back guard.
Figure 2B:
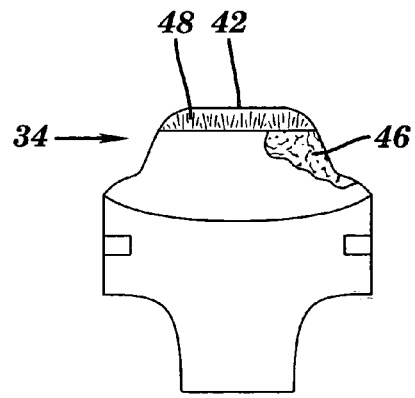
Figure 2C:
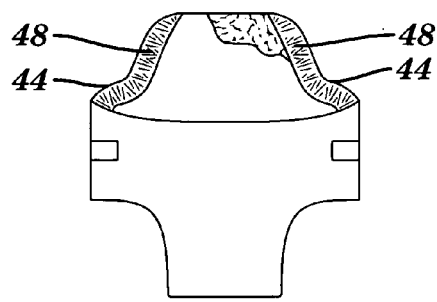
Figure 2D:
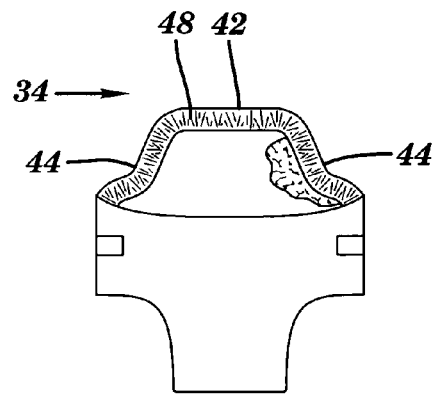

Referring to FIGS. 2B-D, elastic 48 could be used in conjunction with absorbent material 46. Elastic 48 is preferably positioned at any location(s) along a periphery of back guard 34. As shown in FIG. 2B, elastic 48 could be positioned along top portion 42. FIG. 2C shows that elastic 48 could be positioned along curved side portions 44. FIG. 2D demonstrates that elastic 48 could be positioned along the entire periphery of back guard 34 (i.e., along top portion 42 as well as curved side portions 44).

The various positions of elastic 48 on back guard 34 shown in FIGS. 2B-D are not intended to be exhaustive and it should be appreciated that other variations could exist. For example, elastic 48 could be positioned along top portion 42 and/or one curved side portion 44. Moreover, when elastic 48 is implemented, it is preferably positioned at a different location(s) (i.e., separately positioned/located) on back guard 34 than absorbent material 46. Specifically, elastic 48 is positioned along the periphery of back guard 34, while absorbent material is located centrally on back guard 34. Thus, back guard 34 could have two distinct regions: (1) an elastic region; and (2) an absorbent material region.

Figure 2E:
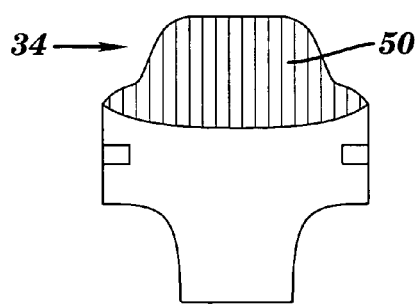

FIG. 2E shows that back guard 34 could also include rigid support structures or boning 50 to provide rigidity and support thereto. Structures 50 are preferably a series of stitches, or are plastic, wood, or metal rod-like articles inserted into back guard 34. Although shown as a series of vertically oriented articles, structures 50 could be implemented in any quantity (e.g., one), and could be horizontally oriented, diagonally oriented, or any combination thereof. Moreover, structures 50 are preferably used in conjunction with absorbent material, and optionally, with any configuration of elastic shown in FIGS. 2B-D.

FIGS. 3A-E show an incontinence article 52 having a back guard 54 in a closed position (when not worn by a user), according to a second embodiment of the present invention is shown. As depicted, back guard 54 includes top portion 62, linear opposing side portions 64, and absorbent material 66. As described above, article 52 includes an impermeable outer cover 58 (shown on front portion 56). Rear portion and front portion 56 are placed in a closed position using any means known in the art. For example, tabs 60 could be used to further couple front portion 56 to rear portion. Tabs 60 could use adhesive, hooks and loops, etc. Moreover, the quantity of tabs shown is not intended to be limiting. For example, article 52 could include four tabs. Back guard 54 is intended to extend from rear portion to the middle back area of the user. As shown, when placed in a closed position without a user, back guard 54 extends well above front portion 56. In previous articles, the rear portion and front portion 56 were approximately parallel when placed in a closed position without a user. Thus, the only way to extend the previous article to the middle back area is to pull the front portion downward while pulling the back portion upward.

Referring to FIGS. 3B-D, elastic 68 could be used in conjunction with absorbent material 66. Preferably, elastic 68 is positioned at any location(s) along a periphery of back guard 54. As shown in FIG. 3B, elastic 68 could be positioned along top portion 62. FIG. 3C shows that elastic 68 could be positioned along side portions 64. FIG. 3D demonstrates that elastic 68 could be positioned along the entire periphery of back guard 54 (i.e., along top portion 62 as well as side portions 64).

The various positions of elastic 68 on back guard 54 shown in FIGS. 3B-D are not intended to be exhaustive and it should be appreciated that other variations could exist. For example, elastic 68 could be positioned on top portion 62 and/or one side portion 64. Moreover, when elastic 68 is implemented, it is preferably positioned at a different location(s) (i.e., separately positioned) on back guard 54 than absorbent material 66. Specifically, elastic 68 is positioned along the periphery of back guard 54, while absorbent material is located centrally on back guard 54. Thus, back guard 54 could have two distinct regions: (1) an elastic region; and (2) an absorbent material region.

FIG. 3E shows that back guard 54 could also include rigid support structure or boning 70 to provide rigidity and support thereto. Structures 70 are preferably a series of stitches, or are plastic, wood, or metal rod-like articles inserted into back guard 54. Although shown as a series of vertically oriented articles, structures 70 could be implemented in any quantity (e.g., one), and could be horizontally oriented, diagonally oriented, or any combination thereof. Moreover, structures 70 are preferably used in conjunction with absorbent material, and optionally, with any configuration of elastic shown in FIGS. 3B-D.

Referring now to FIGS. 4A-E, an incontinence article 72 having a back guard 74 in a closed position (when not worn by a user), according to a third embodiment of the present invention is shown. As depicted, back guard 74 is curved and includes top portion 82, side portions 84, and absorbent material 86. As described above, article 72 includes an impermeable outer cover 80 (shown on front portion 78). Rear portion and front portion 78 are placed in a closed position using any means known in the art. For example, tabs 76 could be used to further couple front portion 78 to rear portion. Tabs 76 could use adhesive, hooks and loops, etc. Moreover, the quantity of tabs shown is not intended to be limiting. For example, article 72 could include four tabs. Back guard 74 is intended to extend from rear portion to the middle back area of the user. As shown, when placed in a closed position without a user, back guard 74 extends well above front portion 78. In previous articles, the rear portion and front portion 78 were approximately parallel when placed in a closed position without a user. Thus, the only way to extend the previous article to the middle back area is to pull the front portion downward while pulling the back portion upward.

Figure 4A:
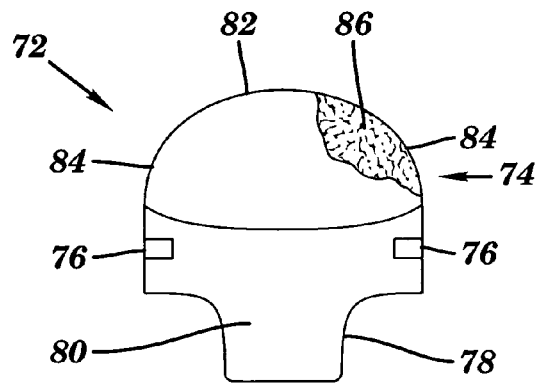
FIGS. 4A-E depict front views of an incontinence article having a back guard.
Figure 4B:
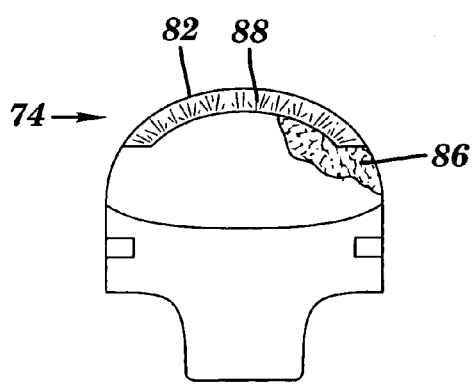
Figure 4C:
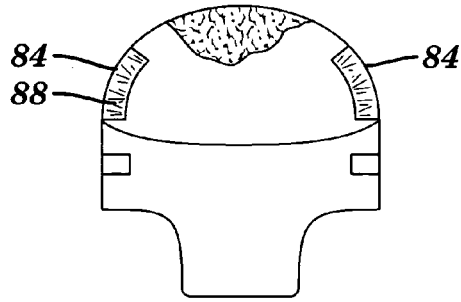
Figure 4D:
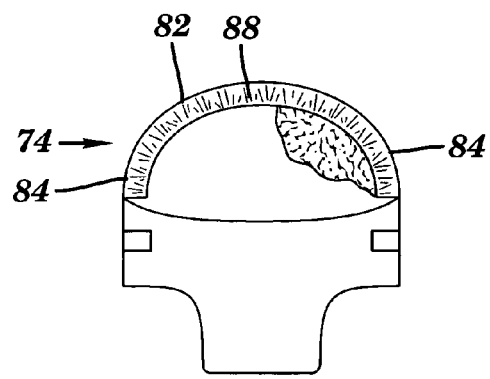

Referring to FIGS. 4B-D, elastic 88 could be used in conjunction with absorbent material 86. Preferably, elastic 88 is positioned at any location(s) along a periphery of back guard 74. As shown in FIG. 4B, elastic 88 could be positioned along top portion 82. FIG. 4C shows that elastic 88 could be positioned along side portions 84. FIG. 4D demonstrates that elastic 88 could be positioned along the entire periphery of back guard 74 (i.e., along top portion 82 as well as side portions 84).

The various positions of elastic 88 on back guard 74 shown in FIGS. 4B-D are not intended to be exhaustive and it should be appreciated that other variations could exist. For example, elastic 88 could be provided on top portion 82 and/or one side portion 84. Moreover, when elastic 88 is implemented, it is preferably positioned at a different location(s) (i.e., separately positioned) on back guard 74 than absorbent material 86. Specifically, elastic 88 is positioned along the periphery of back guard 74, while absorbent material is located centrally on back guard 74. Thus, back guard 74 could have two distinct regions: (1) an elastic region; and (2) an absorbent material region.

Figure 4E:
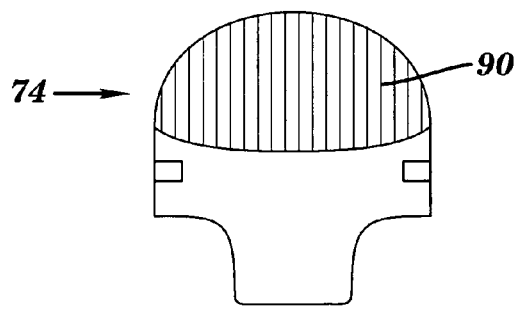

FIG. 4E shows that back guard 74 could also include rigid support structures or boning 90 to provide rigidity and support thereto. Structures 90 are preferably a series of stitches, or are plastic, wood, or metal rod-like articles inserted into back guard 74. Although shown as a series of vertically oriented articles, structures 90 could be implemented in any quantity (e.g., one), and could be horizontally oriented, diagonally oriented, or any combination thereof. Moreover, structures 90 are preferably used in conjunction with absorbent material, and optionally, with any configuration of elastic shown in FIGS. 4B-D.

Referring now to FIGS. 5A-I, an incontinence article 100 having a back guard 102 in a closed position (when not worn by a user), according to a fourth embodiment of the present invention is shown. As depicted, back guard 102 includes: (1) vertical extension 104 having top portion 108; (2) horizontal extensions 106 each having lower portion 110, upper portion 112, and side portion 114; and (3) absorbent material 116. Horizontal extensions 106 cause back guard 102 to have a width greater than a width of rear portion and front portion 118. As described above, article 100 includes an impermeable outer cover 120 (shown on front portion 118). Rear portion and front portion 118 are placed in a closed position using any means known in the art. For example, tabs 122 could be used to further couple front portion 118 to rear portion. Tabs 122 could use adhesive, hooks and loops, etc. Moreover, the quantity of tabs shown is not intended to be limiting. For example, article 100 could include four tabs. Back guard 102 is intended to extend from rear portion to the middle back area of a user. As shown, when placed in a closed position without a user, back guard 102 extends well above front portion 118. In previous articles, the rear portion and front portion 118 were approximately parallel when placed in a closed position without a user. Thus, the only way to extend the previous article to the middle back area is to pull the front portion downward while pulling the back portion upward.

Figure 5A:
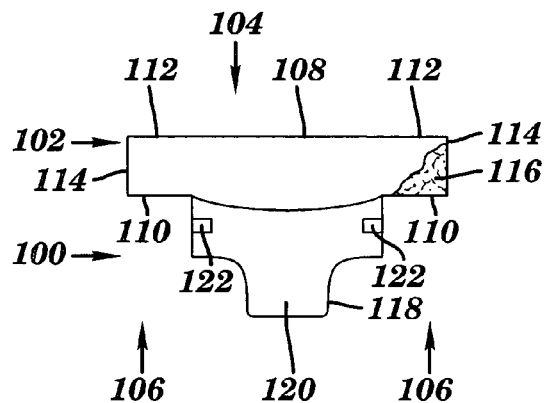
Figure 5B:
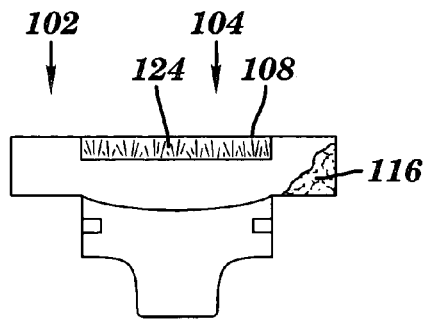
Figure 5C:
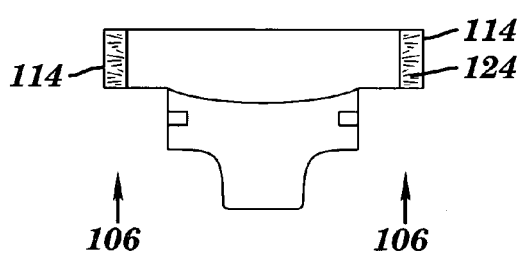
Figure 5D:
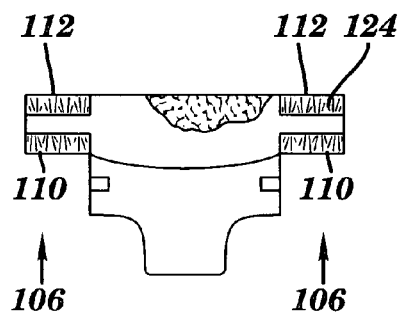
Figure 5E:
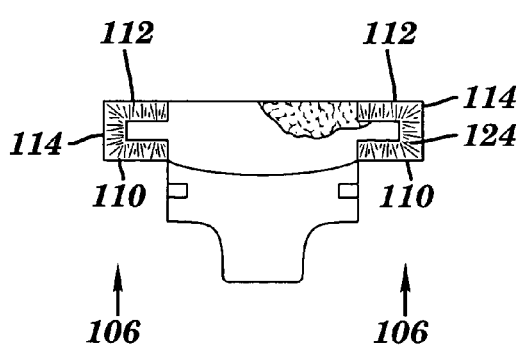
Figure 5F:
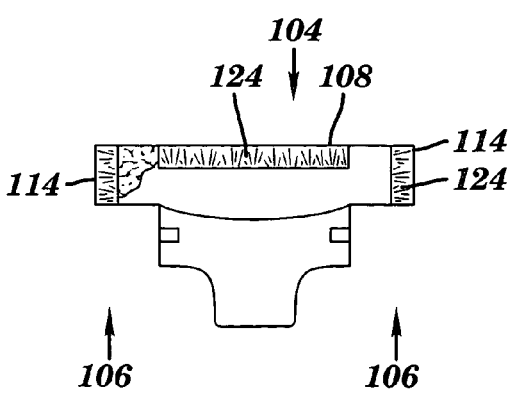

Referring to FIGS. 5B-H, elastic 124 could be used in conjunction with absorbent material 116. Preferably, elastic 124 is positioned at any location(s) along a periphery of back guard 102. As shown in FIG. 5B, elastic 124 could be positioned along top portion 108 of vertical extension 104. FIG. 5C shows that elastic 124 could be positioned along side portions 114 of horizontal extensions 106. FIG. 5D demonstrates that elastic 124 could be positioned along lower portions 110 and upper portions 112 of horizontal extensions 106. FIG. 5E demonstrates that elastic 124 could be positioned along the entire periphery of horizontal extensions 106 (i.e., lower portions 110, upper portions 112, and side portions 114). FIG. 5F demonstrates that elastic 124 could be positioned along side portions 114 of horizontal extensions 106 and top portion 108 of vertical extension 104. FIG. 5G demonstrates that elastic 124 could be positioned along top portion 108 of vertical extension 104 as well as lower portions 110 and upper portions 112 of horizontal extensions 106. FIG. 5H demonstrates that elastic 124 could be positioned along the entire periphery of the back guard 102 (i.e., along top portion 108 of vertical extension 104, and along lower portions 110, upper portions 112, and side portions 114 of horizontal extensions 106).

The examples shown in FIGS. 5B-H are not intended to be exhaustive and it should be appreciated that other combinations of elastic positioning could exist. For example, elastic 124 could be provided in lower portions 110 and side portions 114, but not in upper portions 112. Moreover, when elastic 124 is implemented, it is preferably positioned at a different location(s) (i.e., separately position/located) on back guard 102 than absorbent material 116. Specifically, elastic 124 is positioned along the periphery of back guard 102, while absorbent material is located centrally on back guard 102. Thus, back guard 102 could have two distinct regions: (1) an elastic region; and (2) an absorbent material region.

FIG. 5I shows that back guard 102 could also include rigid support structures or boning 126 to provide rigidity and support thereto. Structures 126 are preferably a series of stitches, or are plastic, wood, or metal rod-like articles inserted into back guard 102. Although shown as a series of vertically oriented articles, structures 126 could be implemented in any quantity (e.g., one), and could be horizontally oriented, diagonally oriented, or any combination thereof. Moreover, structures 126 are preferably used in conjunction with absorbent material, and optionally, with any configuration of elastic shown in FIGS. 5B-H. As further shown in FIG. 5I, horizontal extensions 106 each have a length 107 that is at least 1.0 inches. Preferably, length 107 is approximately 1.0 to 10.0 inches, or any value or range of values there between. It should be understood that these values for length 107 of horizontal extensions 106 are intended to apply to any of FIGS. 5A-I.

Figure 6A:
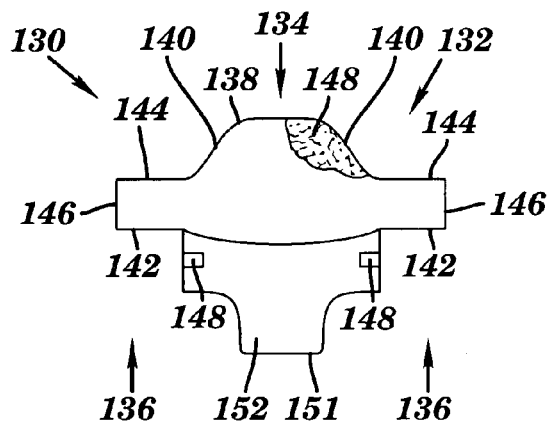
FIGS. 6A-O depict front views of an incontinence article having a back guard.
Figure 6B:
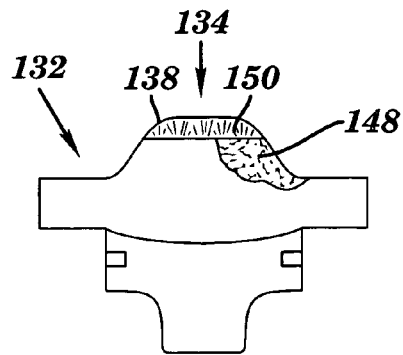
Figure 6C:
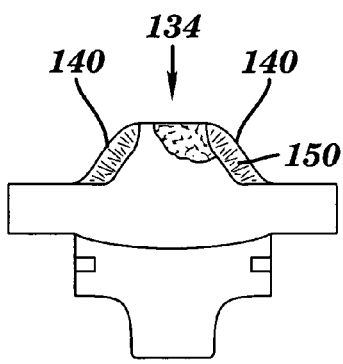
Figure 6D:
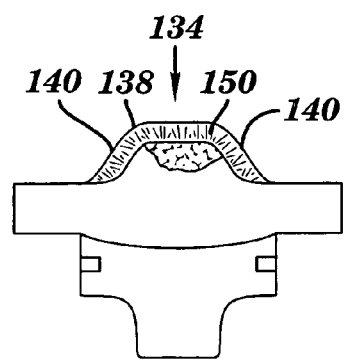
Figure 6E:
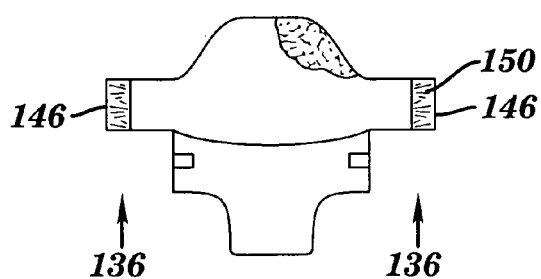
Figure 6F:
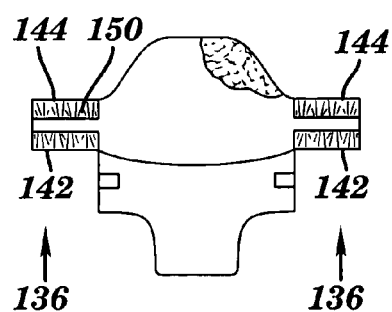
Figure 6G:
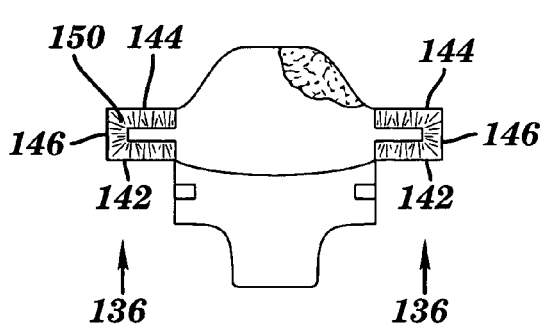
Figure 6H:
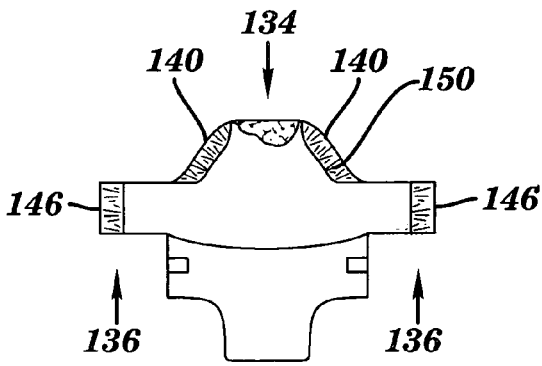
Figure 6I:
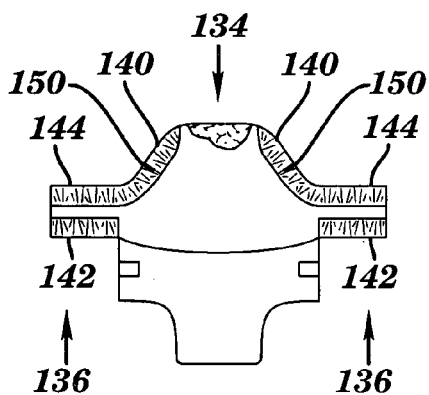
Figure 6J:
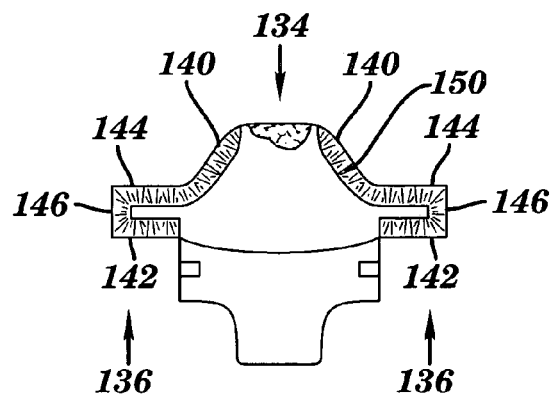
Figure 6K:
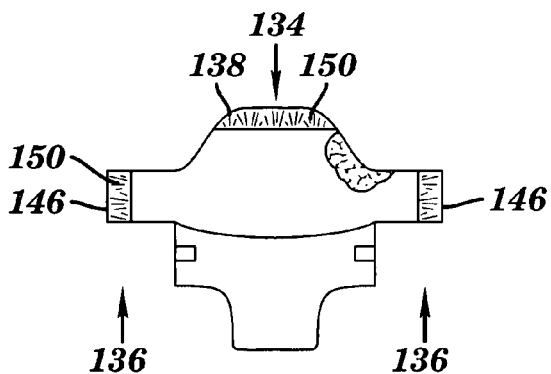
Figure 6L:
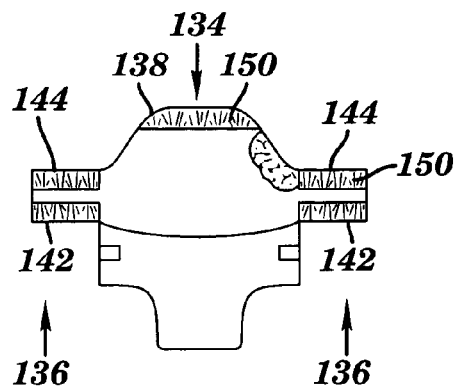
Figure 6M:
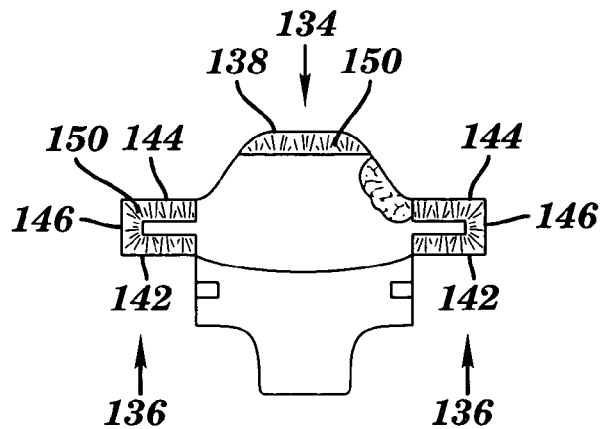
Figure 6N:
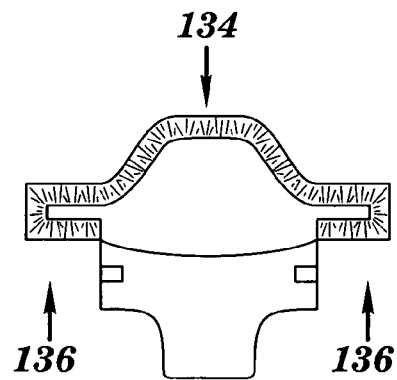
Figure 6O:
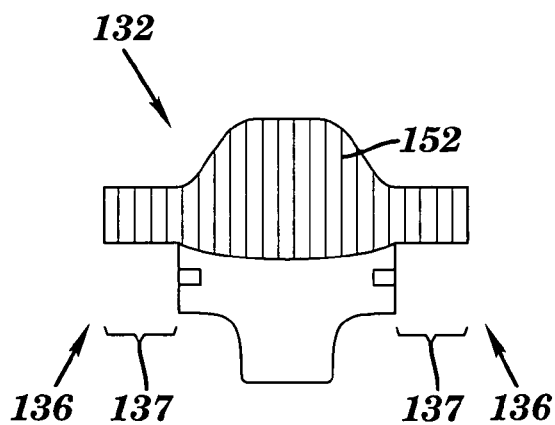

Referring now to FIGS. 6A-O, an incontinence article 130 having a back guard 132 in a closed position (when not worn by a user), according to a fifth embodiment of the present invention is shown. As depicted, back guard 132 includes: (1) vertical extension 134 having top portion 138, and angular side portions 140; (2) horizontal extensions 136 each having lower portion 142, upper portion 144, and side portion 146; and (3) absorbent material 148. Horizontal extensions 136 cause back guard 132 to have a width greater than a width of rear portion and front portion 151. As described above, article 130 includes an impermeable outer cover 152 (shown on front portion 151). Rear portion and front portion 151 are placed in a closed position using any means known in the art. For example, tabs 148 could be used to further couple front portion 151 to rear portion. Tabs 148 could use adhesive, hooks and loops, etc. Moreover, the quantity of tabs shown is not intended to be limiting. For example, article 130 could include four tabs. Back guard 132 is intended to extend from rear portion to the middle back area of a user. As shown, when placed in a closed position without a user, back guard 132 extends well above front portion 151. In previous articles, the rear portion and front portion 151 were approximately parallel when placed in a closed position without a user. Thus, the only way to extend the previous article to the middle back area was to pull the front portion downward while pulling the back portion upward.

Referring to FIGS. 6B-N, elastic 150 could be used in conjunction with absorbent material 148. Preferably, elastic 150 is positioned at any location(s) along a periphery of back guard 132. As shown in FIG. 6B, elastic 150 could be positioned along top portion 138 of vertical extension 134. FIG. 6C shows that elastic 150 could be positioned along angular side portions 140 of vertical extension 134. FIG. 6D demonstrates that elastic 150 could be positioned along the entire periphery (i.e., top portion 138 and angular side portions 140) of vertical extension 134. FIG. 6E demonstrates that elastic 150 could be positioned along side portions 146 of horizontal extensions 136. FIG. 6F demonstrates that elastic 150 could be positioned along lower portions 142 and upper portions 144 of horizontal extensions 136. FIG. 6G demonstrates that elastic 150 could be positioned along the entire periphery (i.e., lower portions 142, upper portions 144, and side portions 146) of horizontal extensions 136. FIG. 6H demonstrates that elastic 150 could be positioned along angular side portions 140 of vertical extension 134, and side portions 146 of horizontal extensions 136. FIG. 6I demonstrates that elastic 150 could be positioned along angular side portions 140 of vertical extension 134, and lower portions 142 and upper portions 144 of horizontal extensions 136. FIG. 6J demonstrates that elastic 150 could be positioned along the entire periphery (i.e., lower portions 142, upper portions 144, and side portions 146) of horizontal extensions 136, and angular side portions 140 of vertical extension 134. FIG. 6K demonstrates that elastic 150 could be positioned along top portion 138 of vertical extension 134, and side portions 146 of horizontal extensions 136. FIG. 6L demonstrates that elastic 150 could be positioned along top portion 138 of vertical extension 134, and lower portions 142 and upper portions 144 of horizontal extensions 136. FIG. 6M demonstrates that elastic 150 could be positioned along top portion 138 of vertical extension 134, and the entire periphery (i.e., lower portions 142, upper portions 144, and side portions 146 of horizontal extensions 136). FIG. 6N demonstrates that elastic 150 could be positioned along the entire periphery (i.e., vertical extension 134 and horizontal extensions 136) of the back guard.

The examples shown in FIGS. 6B-N are not intended to be exhaustive and it should be appreciated that other combinations of elastic positioning could exist. For example, elastic 150 could be provided in lower portions 142 and side portions 146, but not in upper portions 112. Moreover, when elastic 150 is implemented, it is preferably positioned at a different location(s) (i.e., separately position/located) on back guard 132 than absorbent material 148. Specifically, elastic 150 is positioned along the periphery of back guard 132, while absorbent material is located centrally on back guard 132. Thus, back guard 132 could have two distinct regions: (1) an elastic region; and (2) an absorbent material region.

FIG. 6O shows that back guard 132 could also include rigid support structures or boning 152 to provide rigidity and support thereto. Structures 152 are preferably a series of stitches, or are plastic, wood, or metal rod-like articles inserted into back guard 132. Although shown as a series of vertically oriented articles, structures 152 could be implemented in any quantity (e.g., one), and could be horizontally oriented, diagonally oriented, or any combination thereof. Moreover, structures 152 are preferably used in conjunction with absorbent material, and optionally, with any configuration of elastic shown in FIGS. 6B-N. As further shown in FIG. 6O, horizontal extensions 136 each have a length 137 that is at least 1.0 inches. Preferably, length 137 is approximately 1.0 to 10.0 inches, or any value or range of values there between. It should be understood that these values for length 137 of horizontal extensions 136 are intended to apply to any of FIGS. 6A-O

Figure 7A:
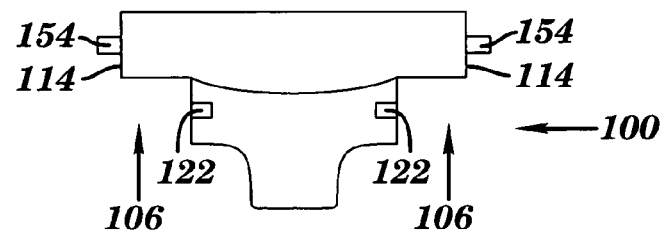
FIGS. 7A-B depict front views the incontinence articles of FIGS. 5A-I in an open position and a first closed position, respectively.
Figure 7B:
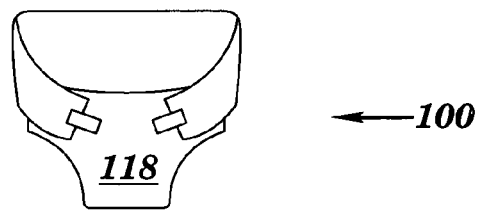
Figure 7C:
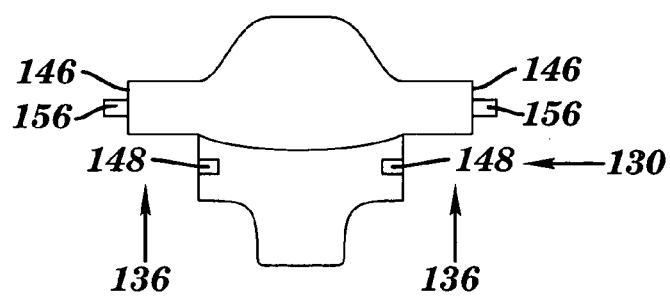
FIGS. 7C-D depict front views the incontinence articles of FIGS. 6A-O in an open position and a first closed position, respectively.
Figure 7D:
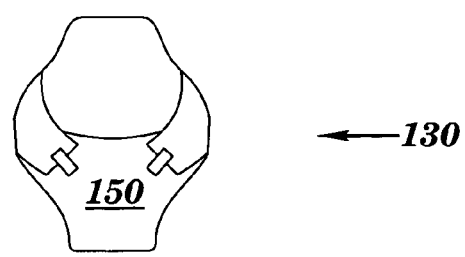

Referring now to FIGS. 7A-B, an example of article 100 of FIGS. 5A-I in a partially closed position and a fully closed position is shown (when not worn by a user). As depicted, article 100 includes tabs 154 on an outer surface of side portions 114 of horizontal extensions 106. FIG. 7B, shows that article 100 can be closed by diagonally coupling horizontal extensions 106 to front portion 118 (in addition to using tabs 122 to couple front portion 118 to rear portion). Specifically, horizontal extensions 106 fold inward and downward so that tabs 154 can couple to front portion 118. FIGS. 7C-D show a similar closing convention for article 130 of FIGS. 6A-O. Specifically, horizontal extensions 136 include tabs 156 on an outer surface of side portions 146.

Horizontal extensions 136 fold inward and downward to diagonally couple to front portion 150. It should be understood that tabs 122 and 148 depicted in FIGS. 7A-D are optional. Specifically, tabs 122 and 148 could be used in conjunction with tabs 154 and 156, or could be substituted for by tabs 154 and 156.

Figure 8A:
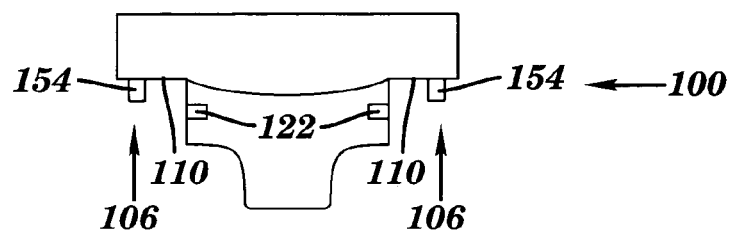
FIGS. 8A-B depict front views the incontinence articles of FIGS. 5A-I in an open position and a second closed position, respectively.
Figure 8B:
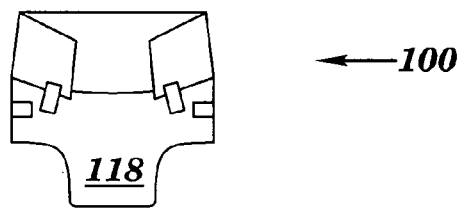
Figure 8C:
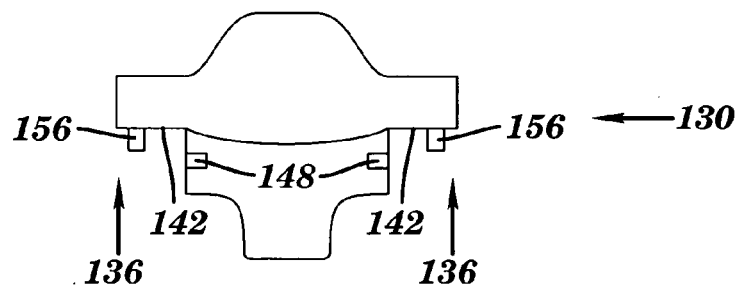
FIGS. 8C-D depict front views the incontinence articles of FIGS. 6A-O in an open position and a second closed position, respectively.
Figure 8D:
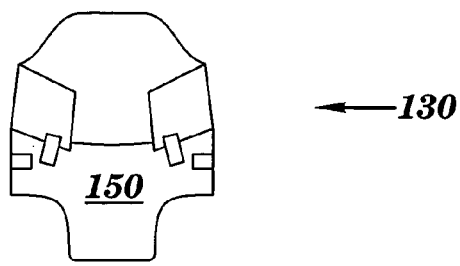

FIGS. 8A-B show an alternative closing convention for article 100. Specifically, tabs 154 are provided on an outer surface lower portions 110 of horizontal extensions 106. Horizontal extensions 106 fold inward and then laterally couple to front portion 118, as shown in FIG. 8B. FIGS. 8C-D shows a similar closing convention for article 130. As show, tabs 156 are attached to an outer surface of lower portions 142 of horizontal extensions 136. Horizontal extensions 136 fold inward for lateral coupling to front portion 150. Similar to FIGS. 7A-7D, it should be understood that tabs 122 and 148 depicted in FIGS. 8A-D are optional. Specifically, tabs 122 and 148 could be used in conjunction with tabs 154 and 156, or could by substituted for by tabs 154 and 156.

It should be understood that the closing conventions shown in FIGS. 7A-D and 8A-D are intended to be illustrative only and other variations could exist. For example, additional tabs could be provided, and/or the tabs could be located on other portions of the articles.

Figure 9:
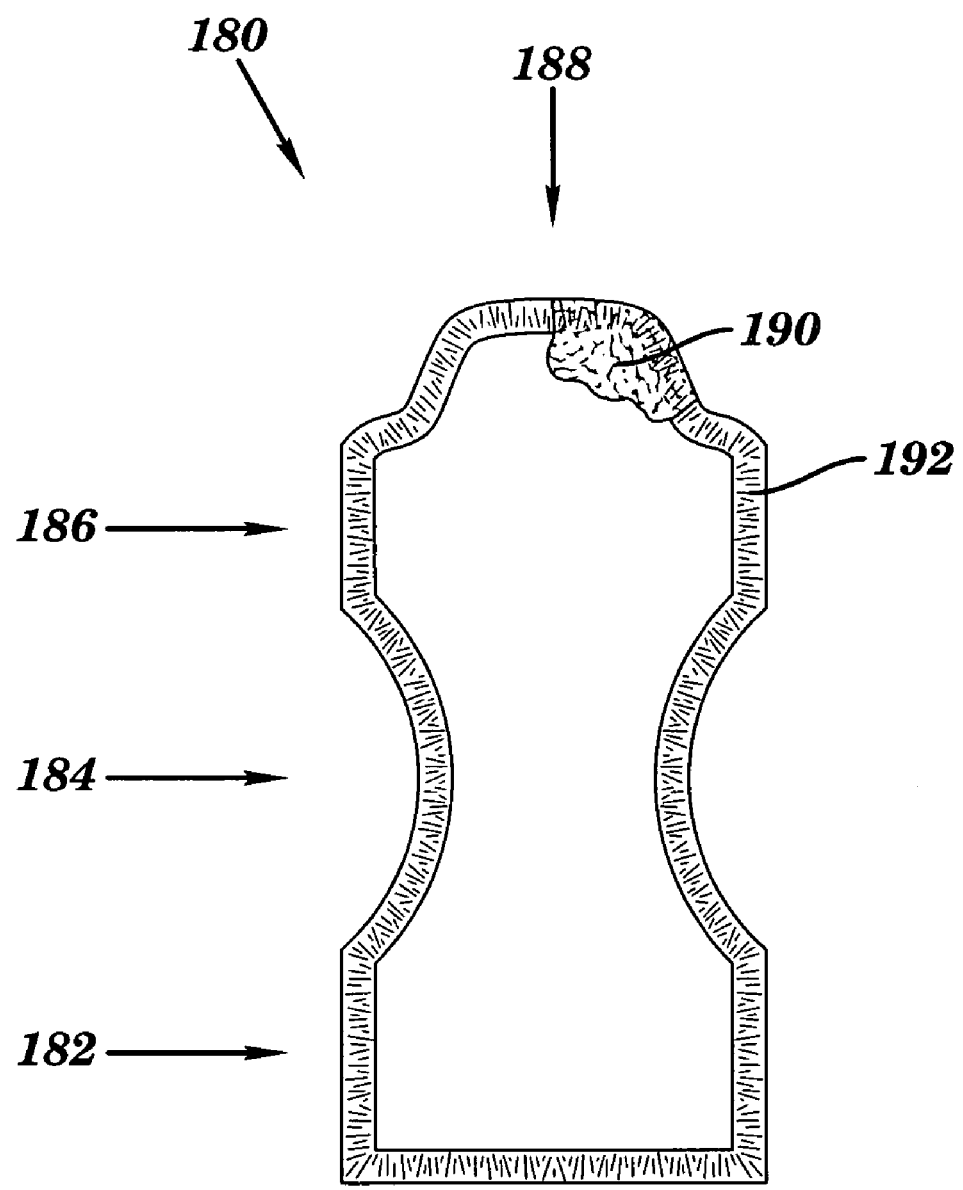
FIG. 9 depicts a plan view of an incontinence article having a back guard.

Referring now to FIG. 9, an article 180 according to a sixth embodiment of the present invention is shown. As depicted, article 180 includes front portion 182, crotch portion 184, rear portion 186, and back guard 188 extending from rear portion 186. Similar to the previous embodiments, back guard 188 extends to the middle back area of the user without having to adjust the positioning of front portion 182. However, under this embodiment of the present invention, elastic 192 is used in the same region(s) as absorbent material 190. Conversely, under the previous embodiments shown in FIGS. 1-8, the absorbent material is used in a different region than the elastic (i.e., the two are separately positioned) to create two distinct regions. However, the embodiment depicted in FIG. 9, shows that absorbent material 190 and elastic 192 can co-exist in the same region (i.e. are commonly positioned). It should be understood that article 180 can include any of the back guards and corresponding elastic arrangements shown and described in conjunction with FIGS. 1-8. Elastic 192 has been shown about the entire periphery of back guard 188 for illustrative purposes only.

Figure 10:
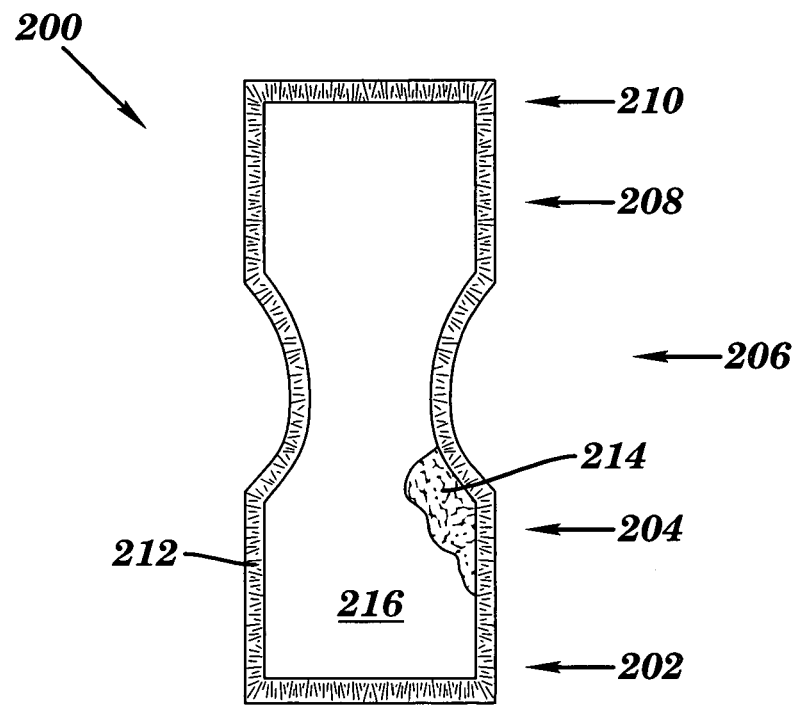
FIG. 10 depicts a front view of an incontinence article having a front guard and a back guard.

Referring now to FIG. 10, an article 200 according to a seventh embodiment of the present invention is shown. In particular, article 200 includes front guard 202 extending from front portion 204, crotch portion 206, back guard 210 extending from rear portion 208, elastic 212, and absorbent material 214. Article 200 preferably has components and construction similar to article 10 of FIG. 1. Specifically, article 200 is preferably a multilayered composite structure having a liquid permeable body-side layer 216, an impermeable outer cover (not shown in FIG. 10), and an absorbent material 214 positioned there between. Moreover, front guard 202 and back guard 210 preferably have the same possible lengths/range of lengths as back guard 18 described above in conjunction with FIG. 1. A purpose of having both a front guard as well as a back guard is to protect both the front and back torso areas of a user.

Figure 11:
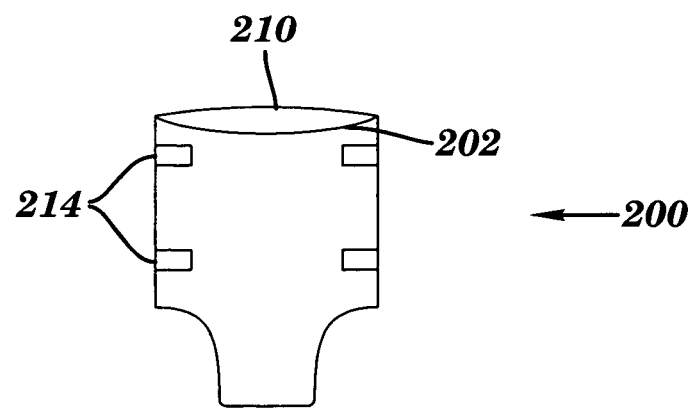
FIG. 11 depicts a front view of the incontinence article of FIG. 10 in a closed position.

FIG. 11 shows article 200 in a closed positioned (when not worn by a user). As can be seen, article 200 is constructed so that back guard 210 will extend to a middle back area of a user, while front guard 202 will extend to a middle chest area of the user. It should be appreciated that front guard 202 and back guard 210 resemble the back guard 62 shown in FIGS. 3A-D for clarity purposes only. For example, front guard 202 and back guard 210 could resemble any back guard shown in the other figures. Moreover, although elastic 212 is shown as being positioned about a periphery of the entire article 200, it should be appreciated that any configuration of elastic could be implemented (as shown and described above in conjunction with FIGS. 1-9). For example, elastic 212 could be eliminated from front guard 202 and/or back guard 210.

As further shown in FIG. 11, article 200 includes tabs 214 for securing front portion 204 and rear portion 208 in a closed position. This is one possible embodiment and is not intended to be limiting. For example, article 200 could include a different quantity of tabs. In addition, front guard 202 and/or back guard 210 could be provided with horizontal and vertical extensions (similar to articles 100 and 130 of FIGS. 5A-I and 6A-O, respectively).

Figure 12:
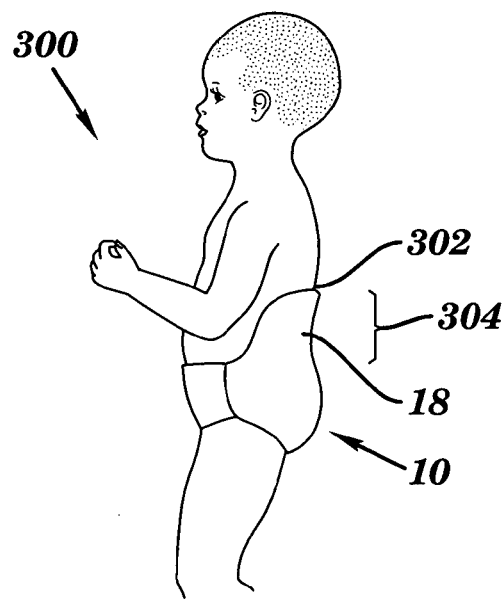
FIG. 12 depicts an incontinence article having a back guard when worn by a user.

FIG. 12 shows article 10 of FIG. 1 as worn by a user 300. It should be understood that article 10 is depicted in FIG. 12 for illustration purposes only and all other embodiments shown and described herein could be worn by user 300. For example, FIG. 12 could depict user 300 wearing article 100 of FIGS. 5A-I. As shown, back guard 18 extends to a middle back area 302 of user 300. Since various users will be different sizes, the length of back guard 18 will vary. Accordingly, back guard 18 can have any length or range of lengths 304 as described above in conjunction with FIG. 1.

Figure 13:
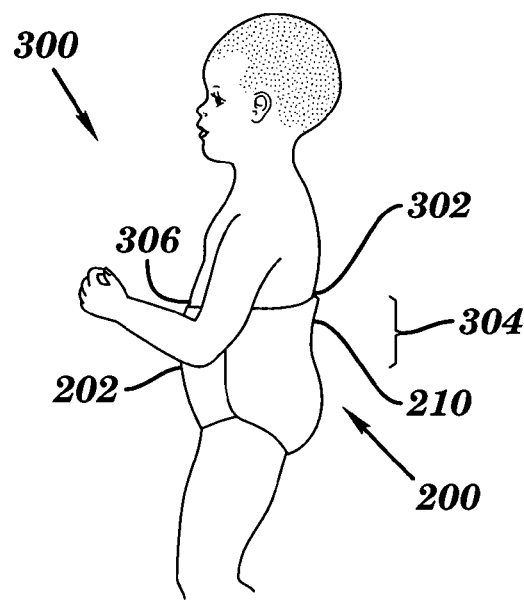
FIG. 13 depicts an incontinence article having a front guard and a back guard when won by a user.

FIG. 13 shows article 200 of FIGS. 10 and 11 as worn by user 300. As depicted front guard 202 and back guard 210 extend to a middle chest area 306 and a middle back area 302, respectively, of user 300. As indicated above, since various users will be different sizes, length 304 of front guard 202 and back guard 210 will vary. Accordingly, front guard 202 and back guard 210 can have any length 304 described above in conjunction with FIG. 1. In addition, front guard 202 and back guard 210 of article 200 can have any of the configurations of the back guards of FIGS. 1-6A-O. For example, front guard 202 and back guard 210 could have vertical and/or horizontal extensions.

Referring now to FIG. 14, an article 400 is shown. In particular, article 400 includes front guard 414 extending from front portion 402, crotch portion 406, back guard 416 extending from rear portion 404 and elastic 408. Article 400 preferably has components and construction similar to article 10 of FIG. 1. and article 200 of FIG. 10. Specifically, article 400 is preferably a multilayered composite structure having a liquid permeable body-side layer 418, an impermeable outer cover, and an absorbent material positioned there between. Moreover, front guard 414 and back guard 416 preferably have the same possible lengths/range of lengths as back guard 18 described above in conjunction with FIG. 1. A purpose of having both a front guard as well as a back guard is to protect both the front and back torso areas of a user.

As further shown in FIG. 14, article 400 includes front bumper 410 positioned on/attached to (i.e., along a top edge of) front guard 414 and back bumper 412 positioned on/attached to (i.e., along a top edge of) back guard 416. Bumpers 410 and 412 further prevents waste material from leaking onto the user. To this extent, front bumper 410 and back bumper 412 can be attached using any known means such as adhesive, hooks and eyes, stitching, as an extension of body side layer 418, etc. As further shown in FIGS. 14-17, bumpers 410 and 412 are block or square in shape. However, it should be understood that other shapes could be implemented (as will be further described below). Bumpers 410 and 412 are preferable formed from an absorbent material such as cotton or the like to maximize waste absorbency.

As shown in FIGS. 15 and 17, it is not necessary for both bumpers 410 and 412 to be provided. For example, FIG. 15 shows that article 400 can be implemented with only front bumper 410, while FIG. 16 demonstrates that article 400 can be implemented with only back bumper 412. FIG. 17 depicts article 400 when worn by a user 420. As shown, article 400 includes front bumper 410 attached to front guard 414, as well as back bumper 412 attached to back guard 416.

Referring now to FIG. 18, an article 500 is shown. In particular, article 500 includes front portion 502, crotch portion 506, back guard 516 extending from rear portion 504 and elastic 512. Article 500 preferably has components and construction similar to article 10 of FIG. 1. and article 200 of FIG. 10. Specifically, article 500 is preferably a multi-layered composite structure having a liquid permeable body-side layer 514, an impermeable outer cover, and an absorbent material positioned there between. Moreover, back guard 516 preferably has the same possible lengths/range of lengths as back guard 18 described above in conjunction with FIG. 1.

As further shown in FIG. 18, article 500 further includes front bumper 508 positioned on/attached to (i.e., along a top edge of) front portion 502 and back bumper 510 positioned on/attached to (i.e., positioned along a top edge of) back guard 516. Bumpers 508 and 510 further prevents waste material from leaking onto the user. To this extent, front bumper 508 and back bumper 510 can be attached using any known means such as adhesive, hooks and eyes, stitching, as an extension of body side layer 514, etc. As further shown in FIGS. 18-21, bumpers 508 and 510 are block or square in shape. However, it should be understood that other shapes could be implemented (as will be further described below). Bumpers 508 and 510 are preferable formed from an absorbent material such as cotton or the like to maximize waste absorbency.

As shown in FIGS. 19 and 20, it is not necessary for both bumpers 508 and 510 to be provided. For example, FIG. 19 shows that article 500 can be implemented with only front bumper 508, while FIG. 20 demonstrates that article 500 can be implemented with only back bumper 510. FIG. 21 depicts article 500 when worn by a user 518. As shown, article 500 includes front bumper 508 attached to front portion 502, as well as back bumper 510 attached to back guard 516.

Referring now to FIG. 22, an article 600 is shown. In particular, article 600 includes front guard 616 extending from front portion 602, crotch portion 606, rear portion 604 and elastic 608. Article 600 preferably has components and construction similar to article 10 of FIG. 1. and article 200 of FIG. 10. Specifically, article 600 is preferably a multi-layered composite structure having a liquid permeable body-side layer 610, an impermeable outer cover, and an absorbent material positioned there between. Moreover, front guard 616 preferably has the same possible lengths/range of lengths as back guard 18 described above in conjunction with FIG. 1.

As further shown in FIG. 22, article 600 further includes front bumper 612 positioned on/attached to (i.e., along a top edge of) front guard 616 and back bumper 614 positioned on/attached to (i.e., along a top edge of) rear portion 604. Bumpers 612 and 614 farther prevents waste material from leaking onto the user. To this extent, front bumper 612 and back bumper 614 can be attached using any known means such as adhesive, hooks and eyes, stitching, as an extension of body side layer 610, etc. As further shown in FIGS. 22-25, bumpers 612 and 614 are block or square in shape. However, it should be understood that other shapes could be implemented (as will be further described below). Bumpers 612 and 614 are preferable formed from an absorbent material such as cotton or the like to maximize waste absorbency.

As shown in FIGS. 23 and 24, it is not necessary for both bumpers 612 and 614 to be provided. For example, FIG. 23 shows that article 600 can be implemented with only front bumper 612, while FIG. 24 demonstrates that article 600 can be implemented with only back bumper 614. FIG. 25 depicts article 600 when worn by a user 618. As shown, article 600 includes front bumper 612 attached to front guard 616, as well as back bumper 5614 attached to rear portion 604.

FIGS. 26-29 depict an article 700 similar to that shown article 400 in FIGS. 14-17. Specifically, article 700 includes front portion 702 having front guard 714, rear portion 704 having back guard 716, crotch portion 706 and elastic 708. Moreover, article 700 preferably has components and construction similar to article 10 of FIG. 1. and article 200 of FIG. 10. Specifically, article 700 is preferably a multilayered composite structure having a liquid permeable body-side layer 718, an impermeable outer cover, and an absorbent material positioned there between. Moreover, front guard 714 and back guard 716 preferably have the same possible lengths/range of lengths as back guard 18 described above in conjunction with FIG. 1.

However, article 700 includes front bumper 710 positioned on/attached to (i.e., along a top edge of) front guard 714 and back bumper 712 positioned on/attached to (i.e., along a top edge of) back guard 716 that are rolls or are rounded in shape (as opposed to blocks). By providing different shaped bumpers, article 700 can be tailored to fit specific body types and shapes. Moreover, similar to article 400, both bumpers 710 and 712 need not be provided, as shown in FIGS. 27 and 28. In any event, bumpers 710 and 712 can be attached using any known means such as adhesives, hooks and eyes, stitching, as an extension of body side layer 718, etc. FIG. 29 depicts article 700 when worn by user 720.

FIGS. 30-33 depict an article 800 similar article 500 of FIGS. 18-21. Specifically, article 800 includes front portion 802, rear portion 804 having back guard 816, crotch portion 806 and elastic 808. Moreover, article 800 preferably has components and construction similar to article 10 of FIG. 1. and article 200 of FIG. 10. Specifically, article 800 is preferably a multilayered composite structure having a liquid permeable body-side layer 818, an impermeable outer cover, and an absorbent material positioned there between. Moreover, back guard 816 preferably has the same possible lengths/range of lengths as back guard 18 described above in conjunction with FIG. 1.

However, article 800 includes front bumper 810 positioned on/attached to (i.e., along a top edge of) front portion 802 and back bumper 812 positioned on/attached to (i.e., along a top edge of) back guard 816 that are rolls or are rounded in shape (as opposed to blocks). By providing different shaped bumpers, article 800 can be tailored to fit specific body types and shapes. Moreover, similar to article 500, both bumpers 810 and 812 need not be provided, as shown in FIGS. 31 and 32. In any event, bumpers 810 and 812 can be attached using any known means such as adhesives, hooks and eyes, stitching, as an extension of body side layer 818, etc. FIG. 33 depicts article 800 when worn by user 820.

FIGS. 34-37 depict an article 850 similar to that shown article 600 in FIGS. 22-25. Specifically, article 850 includes front portion 852 having front guard 858, rear portion 854, crotch portion 856 and elastic 864. Moreover, article 850 preferably has components and construction similar to article 10 of FIG. 1. and article 200 of FIG. 10. Specifically, article 850 is preferably a multilayered composite structure having a liquid permeable body-side layer 868, an impermeable outer cover, and an absorbent material positioned there between. Moreover, front guard 858 preferably has the same possible lengths/range of lengths as back guard 18 described above in conjunction with FIG. 1.

However, article 850 includes front bumper 860 positioned on/attached to (a top edge of) front guard 858 and back bumper 862 positioned on/attached to (i.e., along a top edge of) rear portion 854 that are rolls or are rounded in shape (as opposed to blocks). By providing different shaped bumpers, article 850 can be tailored to fit specific body types and shapes. Moreover, similar to article 600, both bumpers 860 and 862 need not be provided, as shown in FIGS. 35 and 36. In any event, bumpers 860 and 862 can be attached using any known means such as adhesives, hooks and eyes stitching, as an extension of body side layer 868, etc. FIG. 37 depicts article 850 when worn by user 870.

It should be understood that the back guards and/or front guards of FIGS. 14-37 can have any of the configurations set forth in FIGS. 1-13. For example, the front guards and back guards of FIGS. 14-37 could have vertical and/or horizontal extensions. Moreover, it is understood that the front guards and back guards of FIGS. 14-37 could have any configuration of elastic and/or boning as shown in FIGS. 1-13. That is, elastic and/or boning could be implemented in any configuration or not at all. In addition, it should be understood that regardless of the present of a back guard or a front guard, the front bumpers and back bumpers of FIGS. 14-37 are positioned along a top edge of the articles as shown. Such positioning prevents waste from leaking while not effecting the comfort of the user, or the way in which the articles fit.

Referring now to FIG. 38, an article 900 without a front guard or a back guard is shown. In particular, article 900 includes front portion 902, crotch portion 906, rear portion 904 and optional elastic 914. Article 900 preferably has components and construction similar to article 10 of FIG. 1. and article 200 of FIG. 10. Specifically, article 900 is preferably a multilayered composite structure having a liquid permeable body-side layer 916, an impermeable outer cover, and an absorbent material positioned there between.

As further shown in FIG. 22, article 900 further includes front bumper 910 positioned on/attached to (i.e., along a top edge of) front portion 902 and back bumper 912 positioned on/attached to (i.e., along a top edge of) rear portion 904. Bumpers 910 and 912 further prevents waster material from leaking onto the user. To this extent, bumpers 910 and 912 can be attached using any known means such as adhesive, hooks and eyes, stitching, as an extension of body side layer 916, etc. As further shown in FIGS. 38-41, bumpers 910 and 912 are block or square in shape. However, it should be understood that other shapes could be implemented (as will be further described below). Bumpers 910 and 912 are preferable formed from an absorbent material such as cotton or the like to maximize waste absorbency.

As shown in FIGS. 39 and 40, it is not necessary for both bumpers 910 and 912 to be provided. For example, FIG. 39 shows that article 900 can be implemented with only front bumper 910, while FIG. 40 demonstrates that article 900 can be implemented with only back bumper 912. FIG. 25 depicts article 900 when worn by a user 918. As shown, article 900 includes front bumper 910 attached to front portion 902, as well as back bumper 912 attached to rear portion 904. Accordingly, FIGS. 38-41 demonstrate that bumpers 910 and/or 912 can be implemented without front guard or a back guard.

FIGS. 42-45 depict an article 1000 similar to that shown article 900 in FIGS. 38-41 (i.e., without a front guard or a back guard). Specifically, article 1000 includes front portion 1002, rear portion 1004, crotch portion 1006 and optional elastic 1014. Moreover, article 1000 preferably has components and construction similar to article 10 of FIG. 1. and article 200 of FIG. 10. Specifically, article 1000 is preferably a multilayered composite structure having a liquid permeable body-side layer 1016, an impermeable outer cover, and an absorbent material positioned there between.

However, article 1000 includes front bumper 1010 positioned on/attached to (i.e., along a top edge of) front portion 1002 and back bumper 1012 positioned on/attached to (i.e., along a top edge of) rear portion 1004 that are rolls or are rounded in shape (as opposed to blocks). By providing different shaped bumpers, article 1000 can be tailored to fit specific body types and shapes. Moreover, similar to article 900, both bumpers 1010 and 1012 need not be provided, as shown in FIGS. 43 and 44. In any event, bumpers 1010 and 1012 can be attached using any known means such as adhesives, hooks and eyes stitching, as an extension of body side layer 1016, etc. FIG. 45 depicts article 1000 when worn by user 1018.

The foregoing description of the preferred embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

The invention claimed is:

1. An incontinence article, comprising:
   a front portion for wearing adjacent to a front of a user;
   a rear portion joined to the front portion, the rear portion for wearing adjacent to a rear of the user;
   a front guard extending above the rear portion vertically from a waist area of the front portion to a middle chest area of the user; and
   a bumper extending to transversely opposite side edges along a longitudinally outer edge of at least one of the front guard and the rear portion wherein the bumper is absorbent.

2. The article of claim 1, wherein the bumper is positioned along a longitudinally outer edge of the front guard.

3. The article of claim 1, further comprising a back guard extending above the front portion vertically from a waist area of the rear portion to a middle back area of the user, wherein the bumper is attached along a longitudinally outer edge of the back guard.

4. The article of claim 1, wherein the bumper is positioned along the longitudinally outer edge of the front portion.

5. The article of claim 1, wherein the bumper is positioned along the longitudinally outer edge of the rear portion.

6. The article of claim 1, wherein the bumper is a block.

7. The article of claim 1, wherein the bumper is a roll.

8. The article of claim 1, wherein the bumper is absorbent.

9. An incontinence article, comprising:
   a front portion for wearing adjacent to a front of a user, the front portion having a front guard extending vertically from a waist area to a middle chest area of a user;
   a rear portion for wearing adjacent to a rear of the user, the rear portion having a back guard extending vertically from a waist area to a middle back area of a user;
   a crotch portion between the front portion and the rear portion; and a bumper extending to transversely opposite side edges along a longitudinally outer edge of at least one of the front guard and the back guard wherein the bumper is absorbent.

10. The article of claim 9, wherein the bumper is positioned along the longitudinally outer edge of the front guard.

11. The article of claim 9, wherein the bumper is positioned along the longitudinally outer edge of the back guard.

12. The article of claim 9, wherein the bumper is a roll.

13. The article of claim 9, wherein the bumper is a block.

14. The article of claim 9, wherein a first bumper is positioned along the longitudinally outer edge of the front guard, and wherein a second bumper is positioned along the longitudinally outer edge of the back guard.

15. The article of claim 9, wherein the bumper is absorbent.

16. An incontinence article, comprising:
a rear portion for wearing adjacent to a rear of a user;
a front portion for wearing adjacent to a front of a user, the front portion having a front guard extending above the rear portion vertically from a waist area to a middle chest area of a user;
a crotch portion between the front portion and the rear portion; and
a bumper extending to transversely opposite side edges along a longitudinally outer edge of at least one of the front guard and the rear portion wherein the bumper is absorbent.

17. The article of claim 16, wherein the bumper is positioned along the longitudinally outer edge of the front guard.

18. The article of claim 16, wherein the bumper is positioned along the longitudinally outer edge of the rear portion.

19. The article of claim 16, wherein a first bumper is positioned along the longitudinally outer edge of the front guard, and wherein a second bumper is positioned along the longitudinally outer edge of the rear portion.

20. The article of claim 16, wherein the bumper is a roll.

21. The article of claim 16, wherein the bumper is a block.

22. The article of claim 16, wherein the bumper is absorbent.

* * * * *